US008597643B2

(12) United States Patent  (10) Patent No.: US 8,597,643 B2
Barden et al.  (45) Date of Patent: Dec. 3, 2013

(54) ANTIBODIES FOR BINDING TO NON-FUNCTIONAL P2X₇ RECEPTORS IN TRIMERIC FORM

(75) Inventors: Julian Alexander Barden, North Ryde (AU); Angus Gidley-Baird, North Ryde (AU)

(73) Assignee: Biosceptre International Limited (AU)

( * ) Notice: Subject to any disclaimer, the term of this patent is extended or adjusted under 35 U.S.C. 154(b) by 0 days.

(21) Appl. No.: 13/002,647

(22) PCT Filed: Jul. 3, 2009

(86) PCT No.: PCT/AU2009/000869
§ 371 (c)(1),
(2), (4) Date: Jan. 4, 2011

(87) PCT Pub. No.: WO2010/000041
PCT Pub. Date: Jan. 7, 2010

(65) Prior Publication Data
US 2011/0110959 A1    May 12, 2011

(30) Foreign Application Priority Data

Jul. 4, 2008 (AU) .............................. 2008903451

(51) Int. Cl.
C07K 16/30 (2006.01)
A61K 39/395 (2006.01)
G01N 33/53 (2006.01)

(52) U.S. Cl.
USPC .................. 424/130.1; 424/133.1; 424/139.1; 424/141.1; 424/143.1; 435/7.23; 435/7.1; 435/7.2; 435/7.21; 530/387.1; 530/387.3; 530/387.9; 530/388.22

(58) Field of Classification Search
None
See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg | |
| 6,329,503 B1 | 12/2001 | Afar et al. | |
| 6,709,832 B1 | 3/2004 | Von Knebel Doeberitz | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 2004/0067542 A1 | 4/2004 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2009/0215727 A1 | 8/2009 | Douglas | |
| 2010/0036101 A1 | 2/2010 | Gidley-Baird et al. | |
| 2011/0111431 A1 | 5/2011 | Slater et al. | |
| 2011/0177080 A1 | 7/2011 | Barden et al. | |
| 2012/0059151 A1 | 3/2012 | Barden et al. | |
| 2012/0282278 A1 | 11/2012 | Barden et al. | |
| 2013/0171666 A1 | 7/2013 | Gidley-Baird et al. | |

FOREIGN PATENT DOCUMENTS

| | | |
|---|---|---|
| AU | 64184/98 B2 | 6/2011 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |
| WO | WO 03/020762 A1 | 3/2003 |
| WO | WO 2004/092384 A2 | 10/2004 |
| WO | WO 2007/027957 A2 | 3/2007 |
| WO | WO 2008/043145 A2 | 4/2008 |
| WO | WO 2008/043146 A1 | 4/2008 |
| WO | WO 2009/033233 A1 | 3/2009 |
| WO | WO 2009/033234 A1 | 3/2009 |
| WO | WO 2010/000041 A1 | 1/2010 |
| WO | WO 2011/020155 A1 | 2/2011 |
| WO | WO 2011/075789 A1 | 6/2011 |
| WO | WO 2012/031333 A1 | 3/2012 |

OTHER PUBLICATIONS

Mitchell A. Hansen et al., Structural Motif and Characteristics of the Extracellular Domain of P2X Receptors, Biochemical and Biophysical Research Communicaitons 236, pp. 670-675 (1997), Article No. RC976815.
J.A. Barden et al., Specific Detection of Non-Functional Human P2X7 Receptors in HEK293 Cells and B-Lymphocytes, FEBS Letters 538 (2003), pp. 159-162, first published online Feb. 24, 2003.
U.S. Appl. No. 13/518,382, filed Jun. 21, 2012, Barden et al.
U.S. Appl. No. 60/686,770, filed Jun. 2, 2005, Gorodeski et al.
U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).

(Continued)

*Primary Examiner* — Christine J Saoud
*Assistant Examiner* — Jon M Lockard
(74) *Attorney, Agent, or Firm* — Alston & Bird LLP

(57) ABSTRACT

The invention relates to the identification of a novel epitope on non-functional P2X₇ receptors which are implicated in cancer. The epitope includes a region from two adjacent monomers within the three subunit receptor. Antibodies which bind to the epitope and peptides for generating the antibodies are described. The antibodies and peptides are useful in the diagnosis and treatment of cancer.

15 Claims, 7 Drawing Sheets

(56) References Cited

OTHER PUBLICATIONS

Figure 9:
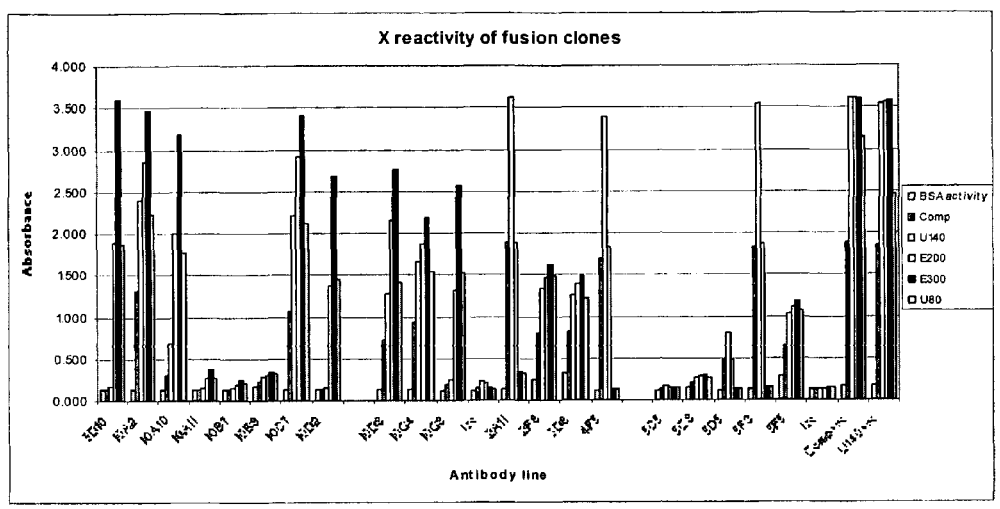

Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al.,"Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report of Sep. 18, 2008 for application EP08156593 (published as EP1961767).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342-C1356, (2005).
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for.
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acids, 25:1271-1276 (2006).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).

Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat × rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "H. sapiens mRNA for P2X7 receptor". [Retrieved from the Internet May 24, 2011 : <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology,125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117.1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al, "A Glu-496 to Ala Polymorphism leads to loss of function of the human P2X7 receptor," J Biol Chem, 276(14):11135-11142, (2001).
Gu et al., "An Arg307 to Gln Polymorphism within the ATP-binding Site Causes Loss of Function of the Human P2X7 Receptor," J Biol Chem, 279 (30):31287-31295, (2004).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2×1)—receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Acad Sci. USA, 90:6444-6448, (1993).
Hopfner et al., "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).
Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled ADP Receptors Mediating Platelet Activation," Thromb and Haemost, 81:111-117, (1999).
Jones, "Critically assessing the state-of-the-art in protein structure prediction,"Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nery Syst, 81:158-163, (2000).
Kim et al., "Differential Assembly of Rat Purinergic P2X7 Receptor in Immune Cells of the Brain and Periphery," J Biol Chem, 276(26):23262-23267, (2001).

(56) References Cited

OTHER PUBLICATIONS

King et al, "Metabotropic receptors for ATP and UTP: exploring the correspondence between native and recombinant nucleotide receptors," TiPS, 19: 506-514, (1998).
Kishore et al., "Cellular localisation of P2Y2 purinoceptor in rat renal inner medulla and lung," Am J Physiol Renal Physiol, 278: F43-F51, (2000).
La Sala et al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(20): 321-330, (2000).
Li et al., "P2X7 Receptor: A Novel Biomarker of Uterine Epithelial Cancers," Cancer Epidemiol Biomarkers Prev, 15(10):1906-1913, (2006).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissue," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11;14)(q13;q32) translocation of B-lymphocytic malignanacy," Blood, 74:1801-1806, (1989).
Nawa et al., "Frequent loss of expression or aberrant alternative splicing of P2XM, a p53-inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 14, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.
PCT International Preliminary Report on Patentability of Jun. 26, 2012 for application PCT/AU2010/001741.
PCT International Search Report for application PCT/AU2010/001741 mailed Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol,199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026 ) mailed Oct. 29, 2012.
Supplementary European Search Report and European Search Opinion for application EP09771858 (published as EP2318438) mailed Oct. 24, 2012.
Supplementary European Search Report of Mar. 4, 2011 for application EP01270623 (published as EP1352085).

(56) References Cited

OTHER PUBLICATIONS

Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now Patent No. 7,183,064), Final Office Action mailed May 9, 2006.
U.S. Appl. No. 10/019,356 (now Patent No. 7,183,064), Non-Final Office Action mailed Jul. 19, 2005.
U.S. Appl. No. 10/019,356 (now Patent No. 7,183,064), Notice of Allowance mailed Oct. 11, 2006.
U.S. Appl. No. 10/019,356 (now Patent No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now Patent No. 7,326,415), Non-Final Office Action mailed Nov. 30, 2006.
U.S. Appl. No. 10/622,313 (now Patent No. 7,326,415), Notice of Allowance and Examiner Interview Summary Record mailed Sep. 5, 2007.
U.S. Appl. No. 10/622,313 (now Patent No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now Patent No. 7,531,171), Non-Final Office Action mailed Sep. 26, 2008.
U.S. Appl. No. 11/968,607 (now Patent No. 7,531,171), Notice of Allowance mailed Jan. 9, 2009.
U.S. Appl. No. 11/968,607 (now Patent No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now Patent No. 7,888,473), Non-Final Office Action mailed Jun. 16, 2010.
U.S. Appl. No. 12/417,989 (now Patent No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now Patent No. 8,067,550), Non-Final Office Action mailed Oct. 1, 2010.
U.S. Appl. No. 12/445,273 (now Patent No. 8,067,550), Notice of Allowance mailed Mar. 30, 2011.
U.S. Appl. No. 12/445,273 (now Patent No. 8,067,550), Notice of Allowance mailed Jul. 8, 2011.
U.S. Appl. No. 12/445,273 (now Patent No. 8,067,550), Requirement for Restriction/Election mailed Aug. 9, 2010.
U.S. Appl. No. 12/677,795 (now Patent No. 8,293,491), Notice of Allowance mailed Jun. 22, 2012.
U.S. Appl. No. 12/677,795 (now Patent No. 8,293,491), Restriction/Election Requirement mailed Oct. 12, 2011.
U.S. Appl. No. 12/677,799, Non-Final Office Action mailed Jun. 21, 2012.
U.S. Appl. No. 12/677,799, Notice of Allowance and Examiner Interview Summary Record mailed Dec. 10, 2012.
U.S. Appl. No. 12/677,799, Requirement for Restriction/Election mailed Feb. 23, 2012.
U.S. Appl. No. 12/878,865 (now Abandoned, Publication No. 2011/0111431), Non-Final Office Action mailed Oct. 20, 2011.
U.S. Appl. No. 12/878,865 (now Abandoned, Publication No. 2011/0111431), Requirement for Restriction/Election mailed Mar. 25, 2011.
U.S. Appl. No. 12/975,341 (now Patent No. 8,080,635), Non-Final Office Action mailed Mar. 24, 2011.
U.S. Appl. No. 12/975,341 (now Patent No. 8,080,635), Notice of Allowance mailed Aug. 17, 2011.
U.S. Appl. No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 12/677,795 (now Patent No. 8,293,491), Non-Final Office Action mailed Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005).
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al ., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11):17, (2000). Abstract.

(56) References Cited

OTHER PUBLICATIONS

Wiley et al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene,16(9):1183-85, (1998).
Gu et al., "Expression of P2X7 purinoceptors on human lymphocytes and monocytes: evidence for nonfunctional P2X 7 receptors," Am J Physiol Cell Physiol, 279:C1189-C1197, (2000).
PCT International Preliminary Report on Patentability of Mar. 12, 2013 for application PCT/AU2011/001166.
PCT International Search Report of Nov. 4, 2011 for application PCT/AU2011/001166.
Roman et al., "Cloning and Pharmacological Characterization of the Dog P2X7 Receptor," British Journal of Pharmacology, 158:1513-1526, (2009).
Supplementary European Search Report and European Search Opinion for application EP10838429 (published as EP2516470) mailed Apr. 13, 2013.
U.S. Appl. No. 12/677,799, Notice of Allowance mailed Jan. 9, 2013.
U.S. Appl. No. 13/518,382, Requirement for Restriction/Election mailed Mar. 21, 2013.
Casset et al., "A peptide mimetic of an anti-CD4 monoclonal antibody by rational design," Biochemical and Biophysical Research Communications, 307:198-205, (2003).
Colman, "Effects of amino acid sequence changes on antibody-antigen interactions," Research in Immunology, A Structural View of Immune Recognition by Antibodies, 55th Forum in Immunology, 145:33-36, (1994).
Maccallum et al, "Antibody-antigen Interactions: Contact Analysis and Binding Site Topography," J. Mol. Biol., 262:732-745, (1996).
Paul, Fundamental Immunology, 3rd Edition, Raven Press, New York, Chapt. 9, pp. 292-295 (1993).
U.S. Appl. No. 13/518,382, Non-Final Office Action mailed Jun. 18, 2013.
U.S. Appl. No. 13/626,833, Non-Final Office Action mailed Jun. 13, 2013.
U.S. Appl. No. 13/766,630, Non-Final Office Action mailed Aug. 19, 2013.
U.S. Appl. No. 13/518,382, Non-Final Office Action mailed Sep. 18, 2013.
Uniprot sequence entry: Accession No. Q4VKH8, "P2X7 isoform H," Jul. 2005. [Retrieved from the Internet Sep. 9, 2013: <URL: http:// www.ncbi.nlm.nih.gov/protein/Q4VKH8>].
Uniprot sequence entry: Accession No. Q4VKH9, "P2X7 isoform G," Jul. 2005. [Retrieved from the Internet Sep. 9, 2013: <URL: http:// www.ncbi.nlm.nih.gov/protein/Q4VKH9>].
Uniprot sequence entry: Accession No. Q4VKI2, "P2X7 isoform D," Jul. 2005. [Retrieved from the Internet Sep. 9, 2013: <URL: http:// www.ncbi.nlm.nih.gov/protein/Q4VKI2>].
Uniprot sequence entry: Accession No. Q4VKI4, "P2X7 isoform B," Jul. 2005. [Retrieved from the Internet Sep. 9, 2013: <URL: http:// www.ncbi.nlm.nih.gov/protein/Q4VKI4>].

Figure 1:

1   MPACCSCSDV FQYETNKVTR IQSMNYGTIK WFFHVIIFSY VCFALVSDKL YQRKEPVISS

61  VHTKVKGIAE VKEEIVENGV KKLVHSVFDT ADYTFPLQGN SFFVMTNFLK TEGQEQRLCP

121 EYPTRRTLCS SDRGCKKGWM DPQSKGIQTG RCVVHEGNQK TCEVSAWCPI EAVEEAPRPA

181 LLNSAENFTV LIKNNIDFPG HNYTTRNILP GLNITCTFHK TQNPQCPIFR LGDIFRETGD

241 NFSDVAIQGG IMGIEIYWDC NLDRWFHHCR PKYSFRRLDD KTTNVSLYPG YNFRYAKYYK

301 ENNVEKRTLI KVFGIRFDIL VFGTGGKFDI IQLVVYIGST LSYFGLAAVF IDFLIDTYSS

361 NCCRSHIYPW CKCCQPCVVN EYYYRKKCES IVEPKPTLKY VSFVDESHIR MVNQQLLGRS

421 LQDVKGQEVP RPAMDFTDLS RLPLALHDTP PIPGQPEEIQ LLRKEATPRS RDSPVWCQCG

481 SCLPSQLPES HRCLEELCCR KKPGACITTS ELFRKLVLSR HVLQFLLLYQ EPLLALDVDS

541 TNSRLRHCAY RCYATWRFGS QDMADFAILP SCCRWRIRKE FPKSEGQYSG FKSPY (SEQ ID NO: 1)

Figure 2

HNYTTRNIL (SEQ ID NO: 2)

Figure 3

GHNYTTRNIL (SEQ ID NO: 3)

Figure 4

DFPGHNYTTRNIL (SEQ ID NO:4)

Figure 5

1   MPACCSCSDV FQYETNKVTR IQSMNYGTIK WFFHVIIFSY VCFALVSDKL YQRKEPVISS

61  VHTKVKGIAE VKEEIVENGV KKLVHSVFDT ADYTFPLQGN SFFVMTNFLK TEGQEQRLCP

121 EYPTRRTLCS SDRGCKKGWM DPQSKGIQTG RCVVHEGNQK TCEVSAWCPI EAVEEAPRPA

181 LLNSAENFTV LIKNNIDFPG HNYTTRNIL (SEQ ID NO:5)

Figure 6

KTTNVSLYPGYNFRYAKYYKENNVEKRTLIKVFGIRFDILVFGTGGKFD (SEQ ID NO: 6)

Figure 7

KYYKENNVEKRTLIKVF (SEQ ID NO: 7)

Figure 7a

GHNYTTRNILP (SEQ ID NO: 8)

Figure 7b

AKYYKENNVEK (SEQ ID NO: 9)

Figure 7c

GHNYTTRNILPGAGAKYYKENNVEK (SEQ ID NO: 10).

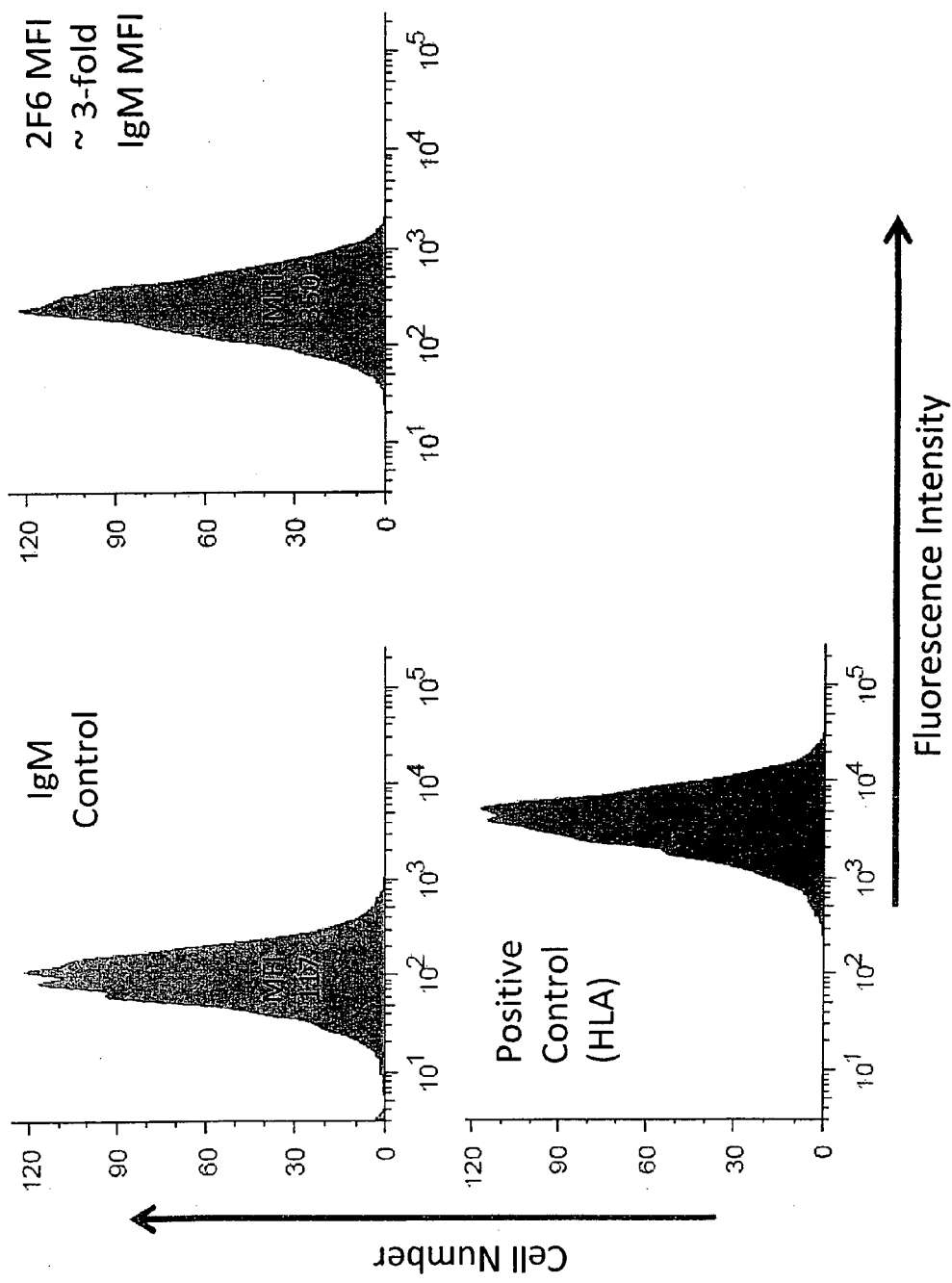

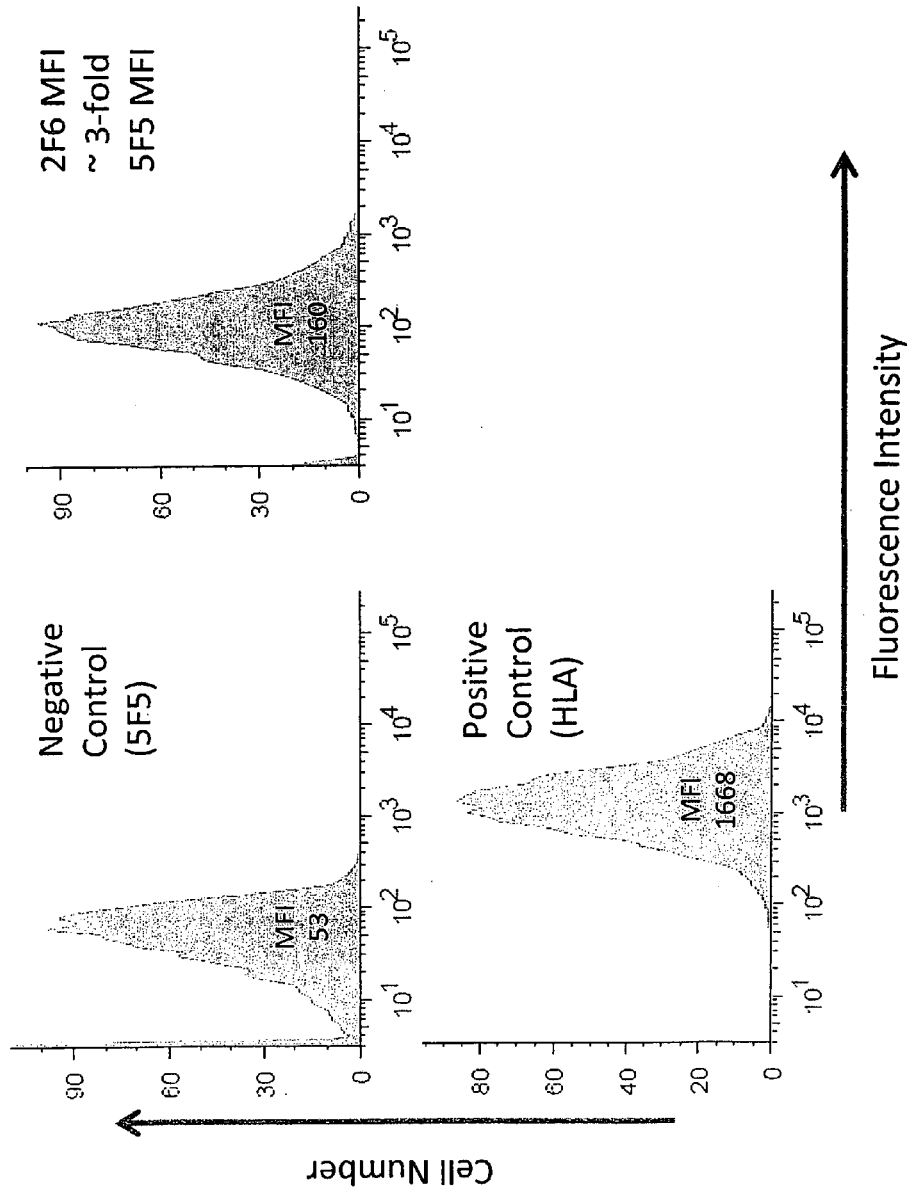
Figure 8b: MAb 2F6 Binding to MCF7 Cells by FACS Analysis

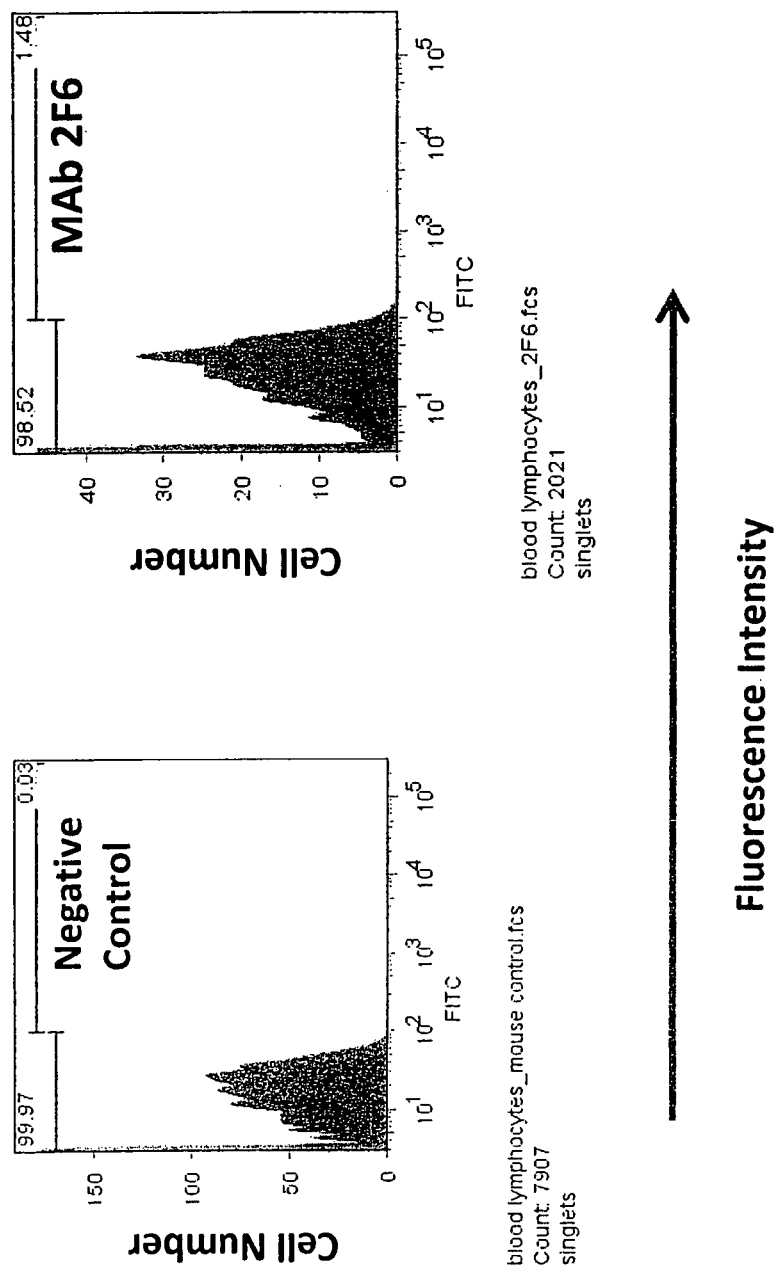
Figure 8c: Non Binding of MAb 2F6 to Functional P2X7 on Human Lymphocytes by FACS Analysis

ANTIBODIES FOR BINDING TO NON-FUNCTIONAL P2X₇ RECEPTORS IN TRIMERIC FORM

CROSS REFERENCE TO RELATED APPLICATIONS

This application is a U.S. National Stage application filed under 35 U.S.C. 371 of International Application No. PCT/AU2009/000869, filed Jul. 3, 2009, which claims priority of Australian Application No. 2008903451, filed Jul. 4, 2008.

REFERENCE TO A SEQUENCE LISTING

This application refers to a "Sequence Listing" listed below, which is provided as a text document. The document is titled PCTAU2009000869_sequence_listing.txt and is 9,041 bytes in size and was created Dec. 28, 2010 and is hereby incorporated by reference in its entirety herein.

FIELD OF THE INVENTION

The present invention relates to peptides, epitopes and production of monoclonal antibodies therefrom.

BACKGROUND OF THE INVENTION

Reference to any prior art in the specification is not and should not be taken as an acknowledgement or any form of suggestion that this prior art forms part of the common general knowledge in Australia or any other jurisdiction or that this prior art could reasonably be expected to be ascertained, understood and regarded as relevant by a person skilled in the art.

Purinergic (P2X) receptors are ATP-gated cation-selective channels. Each receptor is made up of three protein subunits or monomers. To date seven separate genes encoding P2X monomers have been identified: $P2X_1$, $P2X_2$, $P2X_3$, $P2X_4$, $P2X_5$, $P2X_6$, $P2X_7$.

$P2X_7$ receptors are of particular interest as the expression of these receptors is understood to be limited to cells having potential to undergo programmed cell death, such as thymocytes, dendritic cells, lymphocytes, macrophages and monocytes. There is some expression of $P2X_7$ receptors in normal homeostasis, such as on erythrocytes.

Interestingly, a $P2X_7$ receptor containing one or more monomers having a cis isomerisation at Pro210 (according to SEQ ID No: 1 in FIG. 1) and which is devoid of ATP binding function has been found on cells that are understood to be unable to undergo programmed cell death, such as preneoplastic cells and neoplastic cells. This isoform of the receptor has been referred to as a "non functional" receptor.

Antibodies generated from immunisation with a peptide including Pro210 in cis bind to non functional $P2X_7$ receptors. However, they do not bind to $P2X_7$ receptors capable of binding ATP. Accordingly, these antibodies are useful for selectively detecting many forms of carcinoma and haemopoietic cancers and to treatment of some of these conditions.

WO02/057306A1 and WO03/020762A1 both discuss a probe for distinguishing between functional $P2X_7$ receptors and non functional $P2X_7$ receptors in the form of a monoclonal antibody.

Monoclonal antisera have certain serological characteristics not found in polysera that make monoclonal antisera particularly valuable reagents for use in research, diagnosis and therapy. Key amongst these is that monoclonal antibodies generally have an affinity for antigen that is higher than the affinity of most of specificities found in a polysera.

To date it has been very difficult to obtain a hybridoma that generates useful amounts of monoclonal antibody against non functional $P2X_7$ receptors as expressed on live cells, and in particular, monoclonal antibodies that can be used in a range of diagnostic and therapeutic applications. Furthermore, the inventors are not aware of any monoclonal antibodies that have been generated against functional $P2X_7$ receptors on live cells. There is a need for such reagents, particularly for new antibodies capable of discriminating between ATP and non-ATP binding $P2X_7$ receptors on live cells.

Further, as far as the inventors are aware, anti-$P2X_7$ antibodies generally do not discriminate between $P2X_7$ monomers and the trimeric $P2X_7$ receptor formed from these monomers. Antibodies that bind to the trimeric receptor but not to $P2X_7$ monomers would be advantageous for staging a cancer, given that the trimeric receptor is particularly found on advanced neoplastic tissue.

SUMMARY OF THE INVENTION

The invention relates to peptides and epitopes for raising antibodies that bind to non functional $P2X_7$ receptors, but not to functional $P2X_7$ receptors on live cells. The peptides are also useful for raising antibodies that bind to functional $P2X_7$ receptors but not to non functional $P2X_7$ receptors on live cells. The invention also relates to antibodies that bind to these peptides, to compositions containing these peptides, to methods for using the peptides to generate antibodies and to methods of diagnosis and treatment of disease associated with non functional $P2X_7$ receptor expression.

In certain embodiments there is provided an epitope of a $P2X_7$ receptor, the epitope being formed of a first region in the form of a region of a first monomer of a $P2X_7$ receptor; and a second region in the form of a region of a second monomer of the receptor; wherein the first and second regions are formed in the receptor by cis isomerisation of a residue at position 210 of SEQ ID No: 1 of a monomer of the receptor; and wherein the first and second regions are arranged adjacent each other in the receptor thereby permitting binding of an antigen binding site of an anti-$P2X_7$ antibody to the first and second regions forming the epitope.

In other embodiments there is provided a $P2X_7$ receptor having an epitope as described above. Typically one or more of the monomers of the receptor have a cis isomerisation at position 210 of SEQ ID No: 1 of the monomer.

In other embodiments there is provided an antibody for binding to an epitope of a $P2X_7$ receptor, the epitope being formed of a first region in the form of a region of a first monomer of a $P2X_7$ receptor; and a second region in the form of a region of a second monomer of the receptor; wherein the first and second regions are formed in the receptor by cis isomerisation of a residue at position 210 of SEQ ID No: 1 of a monomer of the receptor; and wherein the first and second regions are arranged adjacent each other in the receptor thereby permitting binding of an antigen binding site of the antibody to the first and second regions forming the epitope.

In one embodiment there is provided an immune complex in the form of an epitope as described above bound to an antibody.

In another embodiment there is provided a peptide including an N terminal region and a C terminal region, the N and C terminal regions each being defined by N and C terminal residues, wherein:
  the N terminal region includes a sequence of HNYTTR-NIL (SEQ ID NO: 2) or fragment thereof of at least 4 residues;
  the C terminal region includes a C terminal residue that is proline, alanine, or glycine;

wherein the C terminal residue of the N terminal region is covalently linked to an N terminal residue of the C terminal region;

wherein the C terminal residue of the C terminal region is connected to a further peptide by a linker having a length of about 10 to 40 angstroms;

and wherein said further peptide consists of a sequence KTT-NVSLYPGYNFRYAKYYKENNVEKRT-LIKVFGIRFDILVFGTGGKFD (SEQ ID NO: 6) or fragment thereof of at least 4 residues.

In yet another embodiment there is provided a peptide defined by the formula: (A)(Xn)(B), wherein:
(A) is a sequence of amino acids of GHNYTTRNILP (SEQ ID NO: 8) or a fragment thereof of at least 4 amino acids;
(Xn) is a linker of from 10 to 40 angstroms in length, said linker consisting of one or more amino acid residues;
(B) is a sequence of amino acids of AKYYKENNVEK (SEQ ID NO: 9) or a fragment thereof of at least 4 amino acids.

In further embodiments there is provided a peptide having the following sequence: GHNYTTRNILPGAGAKYYKENNVEK (SEQ ID NO: 10).

In still further embodiments there is provided an immune complex in the form of a peptide described above bound to an antibody. Typically the antibody binds to non functional P2X$_7$ receptors but not to functional P2X$_7$ receptors.

In still further embodiments there is provided a use of a peptide described above for producing an antibody for binding to non functional P2X$_7$ receptors.

In still further embodiments there is provided a use of an antibody described above for determining whether an individual has a cancer.

In still further embodiments there is provided a use of an antibody described above for treating an individual having cancer.

In still further embodiments there is provided a kit including an antibody as described above and optionally:
a peptide as described above;
the kit including written instructions for use in diagnosis or treatment of cancer.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

All of the patents and publications referred to herein are incorporated by reference in their entirety.

The anti-P2X$_7$ antisera against non-functional P2X$_7$ receptors expressed on live cells available at the time of the invention have all been polyclonal.

The inventors have identified an epitope that is exclusively expressed on non ATP-binding P2X$_7$ receptors (otherwise known as "non-functional receptors"). The epitope and peptides forming it have been found to be useful for generating monoclonal antibodies that bind to non-functional P2X$_7$ receptors expressed on live cells.

Live cell binding is important because the expression of the non functional P2X$_7$ receptor in or on cells, examples being epithelial cells, is believed to be a biomarker of many cancers such as epithelial cancers and other conditions. Accordingly, with monoclonal antibodies that bind live cells it becomes possible to provide systemic therapeutics either in the form of the antibody itself, or an antibody-cytotoxic agent conjugate—to a wide range of diseases characterised by expression of non functional P2X$_7$ receptors. It also becomes possible to provide for in vivo imaging and diagnosis or monitoring of diseases characterised by expression of non functional P2X$_7$ receptors.

The inventors have observed from detailed molecular modelling described further herein that the epitope is found only on the P2X$_7$ receptor i.e the trimer formed from P2X$_7$ monomers. More particularly, the epitope spans adjacent P2X$_7$ monomers in the trimeric P2X$_7$ receptor. Individual P2X$_7$ monomers that are not aligned as in a non functional trimeric receptor therefore do not contain the epitope. This advantageously permits one to stage tumours. This is more difficult to do with antibodies that bind to both monomeric P2X$_7$ and the trimeric receptor.

For purposes of interpreting this specification, the following definitions will generally apply and whenever appropriate, terms used in the singular will also include the plural and vice versa. In the event that any definition set forth conflicts with any document incorporated herein by reference, the definition set forth below shall prevail.

"Purinergic receptor" generally refers to a receptor that uses a purine (such as ATP) as a ligand.

"P2X$_7$ receptor" generally refers to a purinergic receptor formed from three protein subunits or monomers, with at least one of the monomers having an amino acid sequence substantially as shown in SEQ ID No:1. To the extent that P2X$_7$ receptor is formed from three monomers, it is a "trimer" or "trimeric". "P2X$_7$ receptor" may be a functional or non functional receptor as described below. "P2X$_7$ receptor" encompasses naturally occurring variants of P2X$_7$ receptor, e.g., wherein the P2X$_7$ monomers are splice variants, allelic variants and isoforms including naturally-occurring truncated or secreted forms of the monomers forming the P2X$_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence P2X$_7$ monomeric polypeptides disclosed herein are mature or full-length native sequence polypeptides comprising the full-length amino acids sequence shown in SEQ ID No:1. In certain embodiments the P2X$_7$ receptor may have an amino acid sequence that is modified, for example various of the amino acids in the sequence shown in SEQ ID No:1 may be substituted, deleted, or a residue may be inserted.

"Functional P2X$_7$ receptor" generally refers to a form of the P2X$_7$ receptor having a binding site or cleft for binding to ATP. When bound to ATP, the receptor forms a pore-like structure that enables the ingress of calcium ions into the cytosol, one consequence of which may be programmed cell death. In normal homeostasis, expression of functional P2X$_7$ receptors is generally limited to cells that undergo programmed cell death such as thymocytes, dendritic cells, lymphocytes, macrophages and monocytes. There may also be some expression of functional $P2X_7$ receptors on erythrocytes.

"Non functional $P2X_7$ receptor" generally refers to a form of a $P2X_7$ receptor in which one or more of the monomers has a cis isomerisation at Pro210 (according to SEQ ID No:1). The isomerisation may arise from any molecular event that leads to misfolding of the monomer, including for example, mutation of monomer primary sequence or abnormal post translational processing. One consequence of the isomerisation is that the receptor is unable to bind to ATP. In the circumstances, the receptor cannot form a pore and this limits the extent to which calcium ions may enter the cytosol. Non functional $P2X_7$ receptors are expressed on a wide range of epithelial and haematopoietic cancers.

"Antibodies" or "immunoglobulins" or "Igs" are gamma globulin proteins that are found in blood, or other bodily fluids of vertebrates that function in the immune system to bind antigen, hence identifying and/or neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a $V_H$ and $V_L$ together forms a "variable region" or "variable domain" including the amino-terminal domains of the heavy or light chain of the antibody. The variable domain of the heavy chain may be referred to as "VH." The variable domain of the light chain may be referred to as "VL." The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each 9-12 amino acids long. The FRs largely adopt a β-sheet configuration and the hypervariable regions form loops connecting, and in some cases forming part of, the β-sheet structure.

"Hypervariable region" refers to the regions of an antibody variable domain which are hypervariable in sequence and/or form structurally defined loops. Generally, antibodies comprise six hypervariable regions; three in the VH (HI, H2, H3), and three in the VL (LI, L2, L3).

"Framework" or "FR" residues are those variable domain residues other than the hypervariable region residues herein defined.

An "intact" or "whole" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof.

"whole antibody fragments including a variable domain" include Fab, Fab', F(ab')$_2$, and Fv fragments; diabodies; linear antibodies, single-chain antibody molecules; and multispecific antibodies formed from antibody fragments.

The "Fab fragment" consists of an entire L chain along with the variable region domain of the H chain ($V_H$), and the first constant domain of one heavy chain ($C_H1$). Each Fab fragment is monovalent with respect to antigen binding, i.e., it has a single antigen-binding site.

A "Fab' fragment" differs from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group.

A "F(ab')$_2$ fragment" roughly corresponds to two disulfide linked Fab fragments having divalent antigen-binding activity and is still capable of cross-linking antigen.

An "Fv" is the minimum antibody fragment which contains a complete antigen-recognition and binding site. This fragment consists of a dimer of one heavy and one light chain variable region domain in tight, non-covalent association.

In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFV" or "scFV" are antibody fragments that comprise the $V_H$ and $V_L$ antibody domains connected to form a single polypeptide chain. Preferably, the scFv polypeptide further comprises a polypeptide linker between the $V_H$ and $V_L$ domains which enables the scFv to form the desired structure for antigen binding.

A "single variable domain" is half of an Fv (comprising only three CDRs specific for an antigen) that has the ability to recognize and bind antigen, although at a lower affinity than the entire binding site "Diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the $V_H$ and $V_L$ domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the $V_H$ and $V_L$ domains of the two antibodies are present on different polypeptide chains. Triabodies and tetrabodies are also generally know in the art.

An "isolated antibody" is one which has been identified and separated and/or recovered from a component of its pre-existing environment. Contaminant components are materials that would interfere with therapeutic uses for the antibody, and may include enzymes, hormones, and other proteinaceous or nonproteinaceous solutes.

A "human antibody" refers to an antibody which possesses an amino acid sequence which corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci have been disabled.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The "monoclonal antibodies" may also be isolated from phage antibody libraries using the techniques.

The term "anti-P2X$_7$ receptor antibody" or "an antibody that binds to P2X$_7$ receptor" refers to an antibody that is capable of binding P2X$_7$ receptor with sufficient affinity such that the antibody is useful as a diagnostic and/or therapeutic agent in targeting P2X$_7$ receptor, typically non functional P2X$_7$ receptor. Preferably, the extent of binding of an P2X$_7$ receptor antibody to an unrelated, P2X$_7$ receptor protein is less than about 10% of the binding of the antibody to P2X$_7$ receptor as measured, e.g., by a radioimmunoassay (RIA). In certain embodiments, an antibody that binds to P2X$_7$ receptor has a dissociation constant (Kd) of <1 µM, <100 nM, <10 nM, <1 nM, or <0.1 nM. An anti non functional P2X$_7$ receptor antibody is generally one having some or all of these serological characteristics and that binds to non functional P2X$_7$ receptors but not to functional P2X$_7$ receptors.

An "affinity matured" antibody is one with one or more alterations in one or more hypervariable region thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art.

A "blocking" antibody" or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Epitope" generally refers to that part of an antigen that is bound by the antigen binding site of an antibody. An epitope may be "linear" in the sense that the hypervariable loops of the antibody CDRs that form the antigen binding site bind to a sequence of amino acids as in a primary protein structure. In certain embodiments, the epitope is a "conformational epitope" i.e. one in which the hypervariable loops of the CDRs bind to residues as they are presented in the tertiary or quaternary protein structure.

In one embodiment there is provided an epitope of a P2X$_7$ receptor the epitope being formed of:

a first region in the form of a region of a first monomer of a P2X$_7$ receptor; and a second region in the form of a region of a second monomer of the receptor;

wherein the first and second regions are formed in the receptor by cis isomerisation of a residue at position 210 of SEQ ID No: 1 of a monomer of the receptor;

and wherein the first and second regions are arranged adjacent each other in the receptor thereby permitting binding of an antigen binding site of an anti-P2X$_7$ antibody to the first and second regions forming the epitope.

Typically the epitope is a conformational epitope. In these embodiments, the first and second regions each define a molecular space that each include one or more residues of SEQ ID No: 1. Typically the first region is one that defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. These residues include Gly 200, His 201, Asn 202, Tyr 203, Thr 204, Thr 205, Arg 206, Asn 207, Ile 208, Leu 209 and Pro210. In one embodiment the first region includes at least one of these residues. Typically the first region includes at least 4 of these residues, although it may be less, for example, 2 or 3, depending on how many residues are presented in the second region. In one embodiment, the first region includes at least 1 pair of residues shown in the Table 1 below:

TABLE 1

| | | | | | | | | |
|---|---|---|---|---|---|---|---|---|
| His 201 | Asn 202 | Tyr 203 | Thr 204 | Thr 205 | Arg 206 | Asn 207 | Ile 208 | Leu 209 |
| Gly 200 | Gly 200 | Gly 200 | Gly 200 | Gly 200 | Gly 200 | Gly 200 | Gly 200 | Gly 200 |
| | Asn 202 | Tyr 203 | Thr 204 | Thr 205 | Arg 206 | Asn 207 | Ile 208 | Leu 209 |
| | His 201 | His 201 | His 201 | His 201 | His 201 | His 201 | His 201 | His 201 |
| | | Tyr 203 | Thr 204 | Thr 205 | Arg 206 | Asn 207 | Ile 208 | Leu 209 |
| | | Asn 202 | Asn 202 | Asn 202 | Asn 202 | Asn 202 | Asn 202 | Asn 202 |
| | | | Thr 204 | Thr 205 | Arg 206 | Asn 207 | Ile 208 | Leu 209 |
| | | | Tyr 203 | Tyr 203 | Tyr 203 | Tyr 203 | Tyr 203 | Tyr 203 |
| | | | | Thr 205 | Arg 206 | Asn 207 | Ile 208 | Leu 209 |
| | | | | Thr 204 | Thr 204 | Thr 204 | Thr 204 | Thr 204 |
| | | | | | Arg 206 | Asn 207 | Ile 208 | Leu 209 |
| | | | | | Thr 205 | Thr 205 | Thr 205 | Thr 205 |
| | | | | | | Asn 207 | Ile 208 | Leu 209 |
| | | | | | | Arg 206 | Arg 206 | Arg 206 |
| | | | | | | | Ile 208 | Leu 209 |
| | | | | | | | Asn 207 | Asn 207 |
| | | | | | | | | Leu 209 |
| | | | | | | | | Ile 208 |

In certain embodiments the first region includes 2 or more pairs of residues shown in Table 2.

The first region may additionally contain one or more peripheral residues that are intimately involved in formation of the ATP binding site on the larger of the two extracellular domain folds. These are Lys 193, Phe 275 and Arg 294. Arg 125 is located in the smaller of the two extracellular domain folds. Thus in certain embodiments, the first region further includes one or more of the following residues of SEQ ID No: 1: Arg 125, Lys 193, Phe 275 and Arg 294. It will be understood that the first region does not consist of these residues alone. That is, the first region, as discussed above, defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. In this context, the Arg 125, Lys 193, Phe 275 and Arg 294 are only provided in addition, but not alternate to for example one or more of the residues Gly 200, His 201, Asn 202, Tyr 203, Thr 204, Thr 205, Arg 206, Asn 207, Ile 208, Leu 209.

Typically the second region is one that defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. These residues include Lys 297, Tyr 298, Tyr 299, Lys 300, Glu 301, Asn 302, Asn 303, Val 304, Glu 305 and Lys 306. In one embodiment the second region includes at least one of these residues. Typically the second region includes at least 4 of these residues, although it may be less, for example, 2 or 3, depending on how many residues are presented in the first region. In one embodiment, the second region includes at least 1 pair of residues shown in the Table 2 below:

TABLE 2

| | | | | | | | | |
|---|---|---|---|---|---|---|---|---|
| Tyr 298 | Tyr 299 | Lys 300 | Glu 301 | Asn 302 | Asn 303 | Val 304 | Glu 305 | Lys 306 |
| Lys 297 | Lys 297 | Lys 297 | Lys 297 | Lys 297 | Lys 297 | Lys 297 | Lys 297 | Lys 297 |
| | Tyr 298 | Tyr 298 | Tyr 298 | Tyr 298 | Tyr 298 | Tyr 298 | Tyr 298 | Tyr 298 |
| | Tyr 299 | Lys 300 | Glu 301 | Asn 302 | Asn 303 | Val 304 | Glu 305 | Lys 306 |
| | | Tyr 299 | Tyr 299 | Tyr 299 | Tyr 299 | Tyr 299 | Tyr 299 | Tyr 299 |
| | | Glu 301 | Glu 301 | Asn 302 | Asn 303 | Val 304 | Glu 305 | Lys 306 |
| | | | Lys 300 | Lys 300 | Lys 300 | Lys 300 | Lys 300 | Lys 300 |
| | | | Glu 301 | Asn 302 | Asn 303 | Val 304 | Glu 305 | Lys 306 |
| | | | | Glu 301 | Glu 301 | Glu 301 | Glu 301 | Glu 301 |
| | | | | Asn 302 | Asn 303 | Val 304 | Glu 305 | Lys 306 |
| | | | | | Asn 302 | Asn 302 | Asn 302 | Asn 302 |
| | | | | | Asn 303 | Val 304 | Glu 305 | Lys 306 |
| | | | | | | Asn 303 | Asn 303 | Asn 303 |
| | | | | | | Val 304 | Glu 305 | Lys 306 |
| | | | | | | | Val 304 | Val 304 |
| | | | | | | | Glu 305 | Lys 306 |
| | | | | | | | | Glu 305 |
| | | | | | | | | Lys 306 |

In certain embodiments the second region includes 2 or more pairs of residues shown in Table 2.

The second region may additionally contain one or more peripheral residues that are intimately involved in formation of the ATP binding site. These are Arg 307 and Lys 311. Thus in certain embodiments, the second region further includes Arg 307 and/or Lys 311. It will be understood that the second region does not consist of these residues alone. That is, the second region, as discussed above, defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. In this context, the Arg 307 and Lys 311 are only provided in addition, but not alternate to for example one or more of the residues Lys 297, Tyr 298, Tyr 299, Lys 300, Glu 301, Asn 302, Asn 303, Val 304, Glu 305 and Lys 306.

In certain embodiments, the epitope is, or includes a linear epitope. Examples include where the first region includes one of the following sequences of SEQ ID No: 1 in Table 3:

TABLE 3

Gly 200 to Tyr 203
His 201 to Thr 204
Asn 202 to Thr 205
Tyr 203 to Arg 206
Thr 204 to Asn 207
Thr 205 to Ile 208
Arg 206 to Leu 209

In these embodiments, the second region of the epitope may include one of the following sequences of SEQ ID No: 1 in Table 4:

TABLE 4

Lys 297 to Lys 300
Tyr 298 to Glu 301
Tyr 299 to Asn 301
Lys 300 to Asn 303
Glu 301 to Val 304
Asn 301 to Glu 305
Asn 303 to Lys 306

In certain embodiments, the first region contains more residues than the second region. In other embodiments, the second region contains more residues than the first region.

The first region and second region may each contain from about 4 to about 10 residues, for example 5, 6, 7, 8 or 9 residues. Where there are more residues in the second region, there may be fewer residues in the first region, ie less than 4, for example 2 or 3. The same applies vice versa.

As described herein, the first and second regions are arranged adjacent each other in the receptor thereby permitting binding of an antigen binding site of an anti-$P2X_7$ antibody to the first and second regions forming the epitope. In more detail, the inventors have found that although located on separate monomers, the first and second regions in combination form an epitope that can be bound by a single antigen binding site of an antibody. Generally, the first and second regions of the epitope are spaced apart no more than about 40 Angstroms. If the distance is greater than this, the antibody binding affinity tends to decrease as the antigen binding site is required to traverse a larger distance across the monomers within the receptor in which case fewer residues are bound. Generally the first and second regions are spaced apart about 10 Angstroms, although greater distances less than 40 Angstroms are possible such as 15, 20, 25, 30, 35 Angstroms.

The epitope described herein may be provided in a substantially purified or isolated form, for example as a fragment of a naturally occurring $P2X_7$ receptor or as a synthetic $P2X_7$ receptor.

In other embodiments there is provided a $P2X_7$ receptor including an epitope as described above. Typically at least one of the monomers of the receptor has an amino acid sequence substantially as shown in SEQ ID No:1. The receptor may be a naturally occurring variant of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides are mature or full-length native sequence polypeptides comprising the full-length amino acids sequence shown in SEQ ID No:1. In certain embodiments the $P2X_7$ receptor may have an amino acid sequence that is modified, for example various of the amino acids in the sequence shown in SEQ ID No:1 may be substituted, deleted, or a residue may be inserted.

Typically the receptor is a non functional $P2X_7$ receptor including an epitope as described above. The cis isomerisation may arise from any molecular event that leads to misfolding of the monomer, including for example, mutation of monomer primary sequence or abnormal post translational processing. In certain embodiments, not all of the monomers of the receptor have a cis isomerisation of a residue at position 210 of a monomer, for example, 1 or 2 of the monomers of the receptor may have a cis isomerisation of a residue at position 210 of SEQ ID No:1.

The receptor may be provided in substantially purified or isolated form, ie it may be isolated from a cell, it may be in the form of a homogenous sample of receptor, whether provided as a solid phase or otherwise.

As described in detail below, the inventors have generated antibodies having an antigen binding site for binding to an epitope described above. Thus in certain embodiments there is provided an antibody for binding to an epitope as described above.

Typically at least one complimentarity determining region ((CDR) (or hypervariable region)) of an antigen binding site (or variable domain) binds to a first region of the epitope and at least one other CDR of that antigen binding site binds to the second region of the epitope. In some embodiments, 2 of the CDRs bind to the first region and the other CDR binds to the second region. In other embodiments, 2 of the CDRs bind to the second region and the other CDR binds to the first region. In some embodiments, one CDR binds the first region, another CDR binds the second region and the remaining CDR is unbound to either first or second region of the epitope.

In certain embodiments there is provided an anti-non functional $P2X_7$ receptor antibody, wherein the antigen binding site of the antibody binds to at least one pair of residues from Table 1 above and to at least one pair of residues from Table 2 above.

In other embodiments there is provided an anti-non functional $P2X_7$ receptor antibody, wherein the antigen binding site of the antibody binds to at least one sequence from Table 3 above and to at least one sequence from Table 4 above.

In other embodiments there is provided an immune complex in the form of an epitope described above bound to an antibody. Typically, the epitope is provided on a $P2X_7$ receptor. All epitopes of the receptor may be bound by antibody or only some, for example, less than three epitopes of the receptor are bound by antibody. The complex may contain more or less antibody molecules than receptors.

As described herein, using a 3 dimensional model of a non functional $P2X_7$ receptor, the inventors have determined a range of peptides that can be used to produce an antibody for binding to the epitope of the invention. Thus, in a certain embodiment, there is provided a peptide including an N-terminal region and a C-terminal region, the N- and C-terminal regions each being defined by N- and C-terminal residues, wherein:

the N-terminal region includes a sequence of one of the following:

| | |
|---|---|
| HNYTTRNIL; | (SEQ ID NO: 2) |
| GHNYTTRNIL; | (SEQ ID NO: 3) |
| DFPGHNYTTRNIL; | (SEQ ID NO: 4) | a fragment of SEQ ID NO: 2 to 4 of at least 4 residues;
the sequence of any one of SEQ ID NOs: 2-4 wherein D residues may be conservatively substituted with an E, N or Q residue; F residues may be conservatively substituted for a Y or W residue; G residues may be conservatively substituted for a A, V, L or I residue; H residues may be conservatively substituted for a K or R residue; N residues may be conservatively substituted for a D, E or Q residue; Y residues may be conservatively substituted for a F or W residue; T residues may be conservatively substituted for C, S or M residue; R residue may be conservatively substituted for a H or K residue; I residue may be conservatively substituted for a G, A, V or L residue; and L residue may be conservatively substituted for a G, A, V or I residue;

```
                                            (SEQ ID NO: 5)
MPACCSCSDVFQYETNKVTRIQSMNYGTIKWFFHVIIFSYVCFALVSDK

LYQRKEPVISSVHTKVKGIAEVKEEIVENGVKKLVHSVFDTADYTFPLQ

GNSFFVMTNFLKTEGQEQRLCPEYPTRRTLCSSDRGCKKGWMDPQSKGI

QTGRCVVHEGNQKTCEVSAWCPIEAVEEAPRPALLNSAENFTVLIKNNI

DFPGHNYTTRNIL;
``` or
a sequence within the sequence of SEQ ID NO. 5 including HNYTTRNIL at the C terminus,
the C-terminal region includes a C-terminal residue that is proline, alanine or glycine, wherein the C-terminal residue of the N-terminal region is covalently linked to an N-terminal residue of the C-terminal region.

The C terminal region may consist of a single amino acid residue in the form of proline in cis conformation. Alternatively it may include other residues located N-terminal of the proline.

Typically, the C-terminal residue of the C-terminal region is connected to a further peptide by a linker having a length of about 10 to 40 Angstroms. In one embodiment the further peptide consists of a sequence of SEQ ID NO: 6 or a fragment thereof of 4 residues or more. In one embodiment the C-terminal region includes a C-terminal residue that is proline in cis conformation.

In one embodiment, the further peptide is derived from $P2X_7$ receptor sequence, and has no more than 594 residues of a $P2X_7$ receptor of SEQ ID NO: 1. In particular, the further peptide may consist of the sequence of SEQ ID NO: 6 or a sequence within the sequence of SEQ ID NO: 6. Examples of these peptides within SEQ ID NO: 6 include those having a sequence described in Table 5 (numbering according to FIG. 1):

TABLE 5

| K281 to K297 |
|---|
| T282 to Y298 |
| T283 to Y299 |
| N284 to K300 |
| V285 to E301 |
| S286 to N302 |
| L287 to N303 |
| Y288 to V304 |
| P289 to E305 |
| G290 to K306 |
| Y291 to R307 |
| N292 to T308 |
| F293 to L309 |
| R294 to I310 |
| Y295 to K311 |
| A296 to V312 |
| K297 to F313 |
| Y298 to G314 |
| Y299 to I315 |
| K300 to R316 |
| E301 to F317 |
| N302 to D318 |

TABLE 5-continued

| N303 to I319 |
|---|
| V304 to L320 |
| E305 to V321 |
| K306 to F322 |
| R307 to G323 |
| T308 to T324 |
| L309 to G325 |
| I310 to G326 |
| K311 to K327 |
| V312 to F328 |
| F313 to D329 |

The peptide shown in Table 5 may have a length of from 6 to 17 residues. In one embodiment, the peptide fragment is K297 to F313 consisting of the sequence of KYYKENNVEKRTLIKVF (SEQ ID NO: 7).

The C-terminal region may be linked or connected to the further peptide by any suitable conjugation reaction that may be used with any suitable linker. The linker may be of a particular length to assist immunogenicity and minimise spatial interference. For example, the linker may have a length of between 10 Å and 40 Å. Preferably the linker has a length of 10 or 20 Å.

The linker may be an amino acid linker of one or more amino acid residues. The term "amino acid linker" however does not intend to imply that such a linker consists exclusively of amino acid residues. The amino acid linker can be any amino acid sequence that does not substantially interfere with the peptide of the invention.

The amino acid residues of the amino acid linker are preferably naturally occurring amino acids or unnatural amino acids, and all-L or all-D or mixtures thereof. For example, the amino acids may be selected from glycine, alanine, leucine, serine, valine and threonine. Preferably the linker consists of one or two amino acids selected from glycine and alanine.

In certain embodiments there is provided a peptide defined by the formula: (A)(Xn)(B), wherein:
(A) is a sequence of amino acids of GHNYTTRNILP (SEQ ID NO: 8) or a fragment thereof of at least 4 amino acids;
(Xn) is a linker of from 10 to 40 angstroms in length, said linker consisting of one or more amino acid residues;
(B) is a sequence of amino acids of AKYYKENNVEK (SEQ ID NO: 9) or a fragment thereof of at least 4 amino acids.

In other embodiments there if provided a having the following sequence: GHNYTTRNILPGAGAKYYKENNVEK (SEQ ID NO: 10).

The peptides of the invention can be made by any number of techniques known in the art including solid phase synthesis and recombinant DNA technology.

As is known in the art, a carrier is a substance that is conjugated to a peptide forming an epitope to enhance immunogenicity. Some carriers do this by binding to multiple carriers so as to provide an antigen of increased molecular weight to the host in which the immune response is to be developed.

Preferred carriers include bacterial toxins or toxoids. Other suitable carriers include the N. meningitides outer membrane protein, albumin such as bovine serum albumin, synthetic peptides, heat shock proteins, Pertussis proteins, protein D from H. influenza and toxin A, B or C from C. difficile.

When the carrier is a bacterial toxin or toxoid, diphtheria or tetanus toxoids are preferred.

Preferably the carrier contains functional groups that can react with the peptide of the invention, or may be modified to be capable of reacting with the peptide.

As mentioned above, the peptides of the invention are useful for generating monoclonal antibodies that bind to non functional P2X$_7$ receptors on live cells, but not to functional P2X$_7$ receptors on live cells. A further advantage is that these peptides can also be used to generate monoclonal antibodies that bind to functional P2X$_7$ receptors on live cells, but not to non functional P2X$_7$ receptors on live cells.

The latter antibodies are particularly important because they can be used to select for individuals for which antibody therapy can be applied systemically. In more detail, the majority of the population contains alleles that control the expression of functional P2X$_7$ receptors on tissues such as lymphoid tissues. Receptor expression in these tissue compartments is understood to be an entirely normal physiology. In contrast, a minority of the population have one or more alleles that control the expression of non functional P2X$_7$ receptor in these tissue compartments. If this latter population was to be provided with antibody that binds non functional receptors expressed on live cells for the treatment of cancer, there is a risk that this therapy might affect the immune system because it would eliminate the lymphoid cells that express non functional receptors.

Accordingly, the antibodies of the invention described herein that bind to functional receptors but not to non functional receptors on live cells are particularly useful for helping select individuals for which antibody therapy should either not be provided or else be provided in an appropriately modified form. Such an assay could be used in conjunction with an identical screen using the antibody to non-functional receptors. In this way patients with functional receptors on lymphoid tissue and patients with non-functional receptors on lymphoid tissue could be separated from patients with low expression levels of receptor, either functional or non-functional. Using each antibody in conjunction enables discrimination of patients who at the least would require closer monitoring as a result of the depletion in their immune cells accompanying treatment of their condition with the therapeutic antibody to non-functional receptor.

In certain embodiments there is provided an antibody for binding to a functional P2X$_7$ receptor, but not a non functional P2X$_7$ receptor expressed on a live cell. In other embodiments there is provided an antibody for binding to a non functional P2X$_7$ receptor, but not a functional P2X$_7$ receptor expressed on a live cell. Typically these antibodies are ones raised against a peptide of the invention.

In certain embodiments the antibodies of the invention may have affinities ranging from $10^{-7}$M to $10^{-13}$M as whole antibody molecules but with a tendency to require $10^{-7}$M if using the hybridoma route preferably as an IgM in order to avoid inhibition of hybridoma growth by the antibodies being produced. These affinities may be increased or decreased using standard techniques known to the skilled worker including antibody affinity maturation.

The antibody may be one obtained from monoclonal or polyclonal antisera. The antibody may be produced by hybridoma or phage display libraries. Monoclonal and polyclonal antisera can be obtained by immunising a host with a peptide of the invention together with an adjuvant according to standard techniques. The resulting sera can be screened using any of a number of serological techniques in which the sera is exposed to receptor expression on live cells.

Using the invention it becomes possible to provide antibodies using recombinant expression. For example, the CDRs of the antibodies generated by immunisation with the peptide of the invention are sequenced, encoding nucleotide sequences are determined and then sub cloned into expression vectors for recombinant synthesis of antibodies. This then provides opportunities to develop chimeric antibodies, i.e. ones containing human variable domains and non human constant domains, humanized antibodies, i.e ones formed by grafting non human CDRs onto a human antibody framework and fully human antibodies.

The antibodies of the invention may be modified with respect to effector function, so as to enhance, e.g., the effectiveness of the antibody in treating cancer. For example, the constant regions of the antibody heavy chain may be altered to the mouse IgG2a, mouse IgG2b or human IgG1 isotype. The antibody thus generated can have improved cellular cytotoxicity (ADCC) or complement mediated cytotoxicity (CMC). In another modification, fucose may be deleted from the Fc region, or sialic acid residues may be introduced into the Fc region. The antibody thus generated may also have enhanced ADCC or enhanced CMC activity. In yet another modification, cysteine residue(s) can be introduced into the Fc region, thereby allowing interchain disulfide bond formation in this region. The homodimeric antibody thus generated can have improved internalization capability and/or increased complement-mediated cell killing and ADCC. Homodimeric antibodies with enhanced anti-tumor activity can also be prepared using heterobifunctional cross-linkers. Alternatively, an antibody can be engineered that has modified or mixed Fc regions and can thereby have enhanced complement lysis and ADCC capabilities.

The antibody may be a whole antibody of any isotype. Where the antibody is an antibody fragment, the antibody fragment is selected from the group consisting of a dAb, Fab, Fd, Fv, F(ab')2, scFv and CDR.

The antibody or fragment may be provided on a solid phase such as a bead, surface or tissue culture vessel.

The antibody or fragment thereof may be provided with a label for detection of binding of the antibody or fragment thereof to receptor expressed on a live cell.

The antibodies and fragments may be labelled for use in medical imaging. Such methods involve chemical attachment of a labelling or imaging agent, such as a radioisotope, which include 67 Cu, 90 Y, 125 I, 131 I, 186 Re, 188Re, 211 At, 212 Bi, administration of the labelled antibody or fragment to a subject in an acceptable carrier, and imaging the labelled antibody or fragment in vivo at the target site. Radio-labelled antibodies or fragments thereof may be particularly useful in in vivo imaging of cancers described herein.

The antibodies can be purified by methods known to the skilled artisan. Purification methods include, among other, selective precipitation, liquid chromatography, HPLC, electrophoresis, chromatofocusing, and various affinity techniques.

In some embodiments, the antibodies disclosed herein may also include multimeric forms of antibodies. For example, antibodies of the invention may take the form of antibody dimers, trimers, or higher-order multimers of monomeric immunoglobulin molecules.

Crosslinking of antibodies can be done through various methods known in the art. For example, crosslinking of antibodies may be accomplished through natural aggregation of antibodies, through chemical or recombinant linking techniques or other methods known in the art. For example, purified antibody preparations can spontaneously form protein aggregates containing antibody homodimers, and other higher-order antibody multimers. In a specific embodiment, crosslinking of antibodies by using a second antibody to bind to the antibodies of interest can be used to form a homodimer. The crosslinker antibody can be derived from a different animal compared to the antibody of interest. For example, a goat anti-mouse antibody (Fab specific) may be added to a mouse monoclonal antibody to form a homodimer. This bivalent crosslinker antibody recognizes the Fab or Fc region of the two antibodies of interest forming a homodimer.

Alternatively, antibody homodimers may be formed through chemical linkage techniques known in the art. Chemical crosslinkers can be homo or heterobifunctional and will covalently bind with two antibodies forming a homodimer. In some embodiments, it is desirable that the chemical crosslinker not interact with the antigen-binding region of the antibody as this may affect antibody function. As will be appreciated by those skilled in the art, antibodies can be crosslinked at the Fab region.

In yet another aspect of the invention there is provided an immune complex formed from the binding of an antibody or fragment thereof as described above to a $P2X_7$ receptor, expressed on a live cell. The receptor may be functional or non functional.

In another embodiment there is provided an immune complex formed from the binding of an antibody or fragment thereof to a peptide described above.

The immune complexes of the invention, including those including an epitope or peptide of the invention are particularly important as detection of in vitro or in vivo is indicative of the presence of, or predisposition to, a disease or condition including preneoplasia and neoplasia.

Further, as described above detection of an immune complex formed from the binding of an antibody or fragment thereof as described above to a functional $P2X_7$ receptor on live cells is an important indicator of a subject's suitability for treatment for a disease or condition characterised by non-functional $P2X_7$ receptor expression. A small percentage of the population normally express $P2X_7$ receptors in the non-functional state on their haematopoietic cells such as thymocytes, dendritic cells, lymphocytes, macrophages and monocytes. It is therefore important to be able to identify this homozygous phenotype for non-functional receptors in subjects who have been identified as being at risk of, or having, cancer for example due to the presence of non-functional $P2X_7$ on other, non-haematopoietic cells.

It is also believed that subjects having a heterozygous non-functional $P2X_7$ receptor phenotype will benefit from identification of the immune complexes of the invention. Treatments that target non-functional $P2X_7$ receptors can be tailored and titrated to take their phenotype into consideration.

These detection methods are described in more detail below.

The antibody or antibody fragment included in the immune complex may be attached to a solid phase, such as a bead or a plate, so that the immune complex is attached to a solid phase when formed. Alternatively, the $P2X_7$ receptor, monomer or fragment thereof included in the immune complex may be attached to a solid phase.

The antibody may be labelled for detection of formation of the immune complex.

The immune complex may further include an antibody or fragment thereof, such as a capture antibody for capture of the immune complex. The further antibody or fragment thereof may bind to the anti $P2X_7$ receptor antibody. Also, the further antibody or fragment thereof may bind to the receptor or fragment thereof.

The further antibody or fragment thereof may be bound to a solid phase such as a phase described above.

The further antibody may be labelled for detection of formation of the immune complex. Examples of labels include fluorophores, dyes, isotopes etc.

In further embodiments there is provided a composition including a peptide or epitope of the invention together with an adjuvant or other molecule for potentiating an immune response to the peptide. The adjuvant may be selective for potentiating a humoral or cellular immune response or for both. In certain embodiments these compositions are useful for vaccination against non functional $P2X_7$ receptor related disease.

In other embodiments there is provided a composition including an antibody of the invention together with a pharmaceutical carrier, excipient or diluent. These compositions are useful for systemic administration of antibodies for treatment of cancer or other non functional $P2X_7$ receptor related disease. In preferred embodiments the antibody is a single domain antibody.

In further embodiments there is provided a method of therapy, diagnosis or monitoring for a disease or condition characterised by expression of non functional $P2X_7$ receptors on epithelial, mesenchymal, germinal, neural, pleural or blood cells, the method comprising administering an antibody to an individual requiring said therapy, diagnosis or monitoring, said antibody being one that binds to non functional $P2X_7$ receptors on live cells but not to functional $P2X_7$ receptors on live cells. In one embodiment the method includes a first step of using an antibody that binds to functional $P2X_7$ receptors on live cells but not to non functional $P2X_7$ receptors.

In certain embodiments there is provided a use of an antibody as described herein for treating an individual having a cancer. In other embodiments there is provided a use of an antibody as described herein in the manufacture of a medicament for treating an individual having a cancer. In other embodiments there is provided a method for treating an individual having a cancer including the step of contacting a tissue of an individual including cancer with an antibody for binding to an epitope or peptide of the invention. The method may be operated in vivo or in vitro.

Typically the cancer is of epithelial (breast, prostate, bowel, lung, skin, cervix, uterine, vaginal), mesenchymal, germinal, neural, pleural or blood origin.

The antibody may be an antigen binding site, immunoglobulin variable domain, antibody, Fab, dab, scFv, diabody, triabody, fusion protein, conjugate or pharmaceutical composition as described above.

Dosage amount, dosage frequency, routes of administration etc are described in detail below.

In another embodiment there is provided a pharmaceutical composition including an antigen binding site for binding to an epitope or peptide of the invention or immunoglobulin variable domain, antibody, Fab, dab, scFv, diabody, triabody, fusion protein or conjugate including the antigen binding site and a pharmaceutically acceptable carrier, diluent or excipient.

Methods of preparing and administering antibodies to a subject in need thereof are well known to, or are readily determined by those skilled in the art. The route of administration may be, for example, oral, parenteral (e.g. intravenous, intraarterial, intraperitoneal, intramuscular, subcutaneous, rectal or vaginal), by inhalation or topical. One form for administration would be a solution for injection, in particular for intravenous or intraarterial injection or drip, comprising a buffer (e.g. acetate, phosphate or citrate buffer), a surfactant (e.g. polysorbate), optionally a stabilizer agent (e.g. human albumin). In other methods antibodies can be delivered directly to the site of disease thereby increasing the exposure of the diseased cell or tissue to the antibody.

Preparations for parenteral administration includes sterile aqueous (aqueous carriers include water, alcoholic/aqueous solutions, emulsions or suspensions, including saline and buffered media) or non-aqueous (non-aqueous solvents are propylene glycol, polyethylene glycol, vegetable oils such as olive oil, and injectable organic esters such as ethyl oleate) solutions, suspensions, and emulsions. Pharmaceutically acceptable carriers include 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., antigen binding site) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed disorders.

Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of certain disorders with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen binding sites with different binding specificities are administered simultaneously, in which case the dosage of each antigen binding sites administered falls within the ranges indicated.

The antibody for binding to the epitope or peptide of the invention can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 μg/ml and in some methods 25-300 μg/ml. Alternatively, the antibody can be administered as a sustained release formulation, in which case less frequent administration is required. Dosage and frequency vary depending on the half-life of the antibody in the patient. The half-life of an antibody can also be prolonged via fusion to a stable polypeptide or moiety, e.g., albumin or PEG. In general, humanized antibodies show the longest half-life, followed by chimeric antibodies and nonhuman antibodies. In one embodiment, the antibody can be administered in unconjugated form. In another embodiment the antibody can be administered multiple times in conjugated form.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease.

Therapeutic agents can be administered by parenteral, topical, intravenous, oral, subcutaneous, intraarterial, intracranial, intraperitoneal, intranasal or intramuscular means for prophylactic and/or therapeutic treatment, in some methods, agents are injected directly into a particular tissue where non-functional $P2X_7$ receptor cells have accumulated, for example intracranial injection. Intramuscular injection or intravenous infusion are preferred for administration of antibody.

An antibody can optionally be administered in combination with other agents that are effective in treating the disorder or condition in need of treatment (e.g., prophylactic or therapeutic).

In another embodiment there is provided a kit or article of manufacture including an antigen binding site, immunoglobulin variable domain, antibody, Fab, dab, scFv, diabody, triabody, fusion protein, conjugate or pharmaceutical composition as described above.

In other embodiments there is provided a kit for use in a therapeutic application mentioned above, the kit including:
  a container holding a therapeutic composition in the form of one or more of an antigen binding site, immunoglobulin variable domain, antibody, Fab, dab, scFv, diabody, triabody, fusion protein, conjugate or pharmaceutical composition;
  a label or package insert with instructions for use.

In certain embodiments the kit may contain one or more further active principles or ingredients for treatment of a cancer or for preventing a cancer-related complication described above.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used to treat a cancer or to prevent a complication stemming from cancer.

The kit may comprise (a) a therapeutic composition; and (b) a second container with a second active principle or ingredient contained therein. The kit in this embodiment of the invention may further comprise a package insert indicating that the and other active principle can be used to treat a disorder or prevent a complication stemming from cancer. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments there is provided a use of an antibody as described herein for determining whether an individual has a cancer. In other embodiments there is provided a use of an antibody as described herein in the manufacture of means for determining whether an individual has a cancer. In other embodiments there is provided a method for determining whether an individual has cancer including the step of contacting a tissue of an individual for which cancer is to be determined with an antibody according to the invention in conditions for forming an immune complex according to the invention and determining whether the immune complex has been formed, whereby the formation of an immune complex determines that the individual has a cancer. The method may be operated in vivo or in vitro.

In one embodiment, the antibody is in the form of an antigen binding site, immunoglobulin variable domain, antibody, Fab, dab, scFv, diabody, triabody, fusion protein, conjugate or diagnostic composition as described above and detecting for the binding of the reagent with the tissues or cells.

For in situ diagnosis, the antigen binding site or any active and functional part thereof may be administered to the organism to be diagnosed by methods known in the art such as, for example, intravenous, intranasal, intraperitoneal, intracerebral, intraarterial injection such that a specific binding between an antigen binding site according to the invention with an eptitopic region on the non-functional $P2X_7$ receptor may occur. The antibody/antigen complex may conveniently be detected through a label attached to the antigen binding site or a functional fragment thereof or any other art—known method of detection.

The immunoassays used in diagnostic applications according to the invention and as described herein typically rely on labelled antigens, antibodies, or secondary reagents for detection. These proteins or reagents can be labelled with compounds generally known to those of ordinary skill in the art including enzymes, radioisotopes, and fluorescent, luminescent and chromogenic substances including, but not limited to colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antigen binding site. For example, the antibody may be conjugated to biotin and the antigen binding site-biotin conjugate detected using labelled avidin or streptavidin. Similarly, the antibody may be conjugated to a hapten and the antibody-hapten conjugate detected using labelled anti-hapten antibody.

Current immunoassays utilize a double antibody method for detecting the presence of an analyte, wherein, the antibody is labeled indirectly by reactivity with a second antibody that has been labeled with a detectable label. The second antibody is preferably one that binds to antibodies of the animal from which the antibody is derived. In other words, if the antibody is a mouse antibody, then the labeled, second antibody is an anti-mouse antibody. For the antibody to be used in the assay described herein, this label is preferably an antibody-coated bead, particularly a magnetic bead. For the antigen binding site to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antigen binding site and the analyte. According to one embodiment of the present invention, the presence of the non-functional $P2X_7$ receptor is determined using a pair of antigen binding sites, each specific for $P2X_7$ receptor protein. One of said pairs of antigen binding sites is referred to herein as a "detector antigen binding site" and the other of said pair of antigen binding sites is referred to herein as a "capture antigen binding site". The antigen binding site of the present invention can be used as either a capture antigen binding site or a detector antigen binding site. The antigen binding site of the present invention can also be used as both capture and detector antigen binding site, together in a single assay. One embodiment of the present invention thus uses the double antigen binding site sandwich method for detecting non-functional $P2X_7$ receptor in a sample of biological fluid. In this method, the analyte (non-functional $P2X_7$ receptor protein) is sandwiched between the detector antigen binding site and the capture antigen binding site, the capture antigen binding site being irreversibly immobilized onto a solid support. The detector antigen binding site would contain a detectable label, in order to identify the presence of the antigen binding site-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antigen binding sites to solid phases are also well known to those of ordinary skill in the art. More recently, a number of porous material such as nylon, nitrocellulose, cellulose acetate, glass fibers and other porous polymers have been employed as solid supports In another embodiment there is provided a diagnostic composition including an antigen binding site, immunoglobulin variable domain, antibody, Fab, dab, scFv, diabody, triabody, fusion protein or conjugate as described above, a diluent and optionally a label.

It is preferred that the antibody to be employed in a diagnostic composition are detectably labeled. A variety of techniques are available for labeling biomolecules, are well known to the person skilled in the art and are considered to be within the scope of the present invention. There are many different labels and methods of labeling known to those of ordinary skill in the art. Examples of the types of labels which can be used in the present invention include enzymes, radio-isotopes, colloidal metals, fluorescent compounds, chemiluminescent compounds, and bioluminescent compounds.

Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, etc. are well known in the art.

Detection methods comprise, but are not limited to, autoradiography, fluorescence microscopy, direct and indirect enzymatic reactions, etc. Commonly used detection assays comprise radioisotopic or non-radioisotopic methods. These comprise, inter alia, Westernblotting, overlay-assays, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay), and CLIA (Chemioluminescent Immune Assay).

In another embodiment there is provided a kit or article of manufacture including an antigen binding site, immunoglobulin variable domain, antibody, Fab, dab, scFv, diabody, triabody, fusion protein, conjugate or a diagnostic composition as described above.

In other embodiments there is provided a kit for use in a diagnostic application mentioned above, the kit including:
an antibody according to the invention and optionally:
a peptide according to the invention;
a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a diagnostic composition which is effective for detection of cancer and may have a sterile access port (for example the container may be an intravenous solution bag or a vial having a stopper pierceable by a hypodermic injection needle). The label or package insert indicates that the diagnostic composition is used for detecting the condition of choice. In one embodiment, the label or package insert includes instructions for use and indicates that the diagnostic composition can be used to detect a cancer.

The kit may comprise (a) a diagnostic composition; and (b) a second container with a second diagnostic agent or second label contained therein. It may further include other materials desirable from a commercial and user standpoint, including other buffers, diluents, filters etc.

EXAMPLE 1

Determining a Three Dimensional Model of Non Functional $P2X_7$ Receptor to Identify Putative Epitopes for Antibody Binding $P2X_7$ monomer structure was based on the modelling performed by Hansen et al. 1998 (Hansen, M. A., Barden, J. A., Balcar, V. J., Keay, K. A., Bennett, M. R. (1997) Biochem. Biophys. Res. Commun. 236, 670-675. Structural motif and characteristics of the extracellular domain of P2X receptors) in which structural homology was determined between P2X subtypes. Further structural homology was obtained with the Ser transferase structure in the PDB data base as it applied to the larger of the two extracellular domains identified in Hansen supra.

This model became the basis for the identification of the residues crucial for binding ATP. These identified residues were altered to Ala using site directed mutagenesis and the mutated receptors were expressed in HEK cells for the purpose of measuring function of the $P2X_7$ channel/pore.

The critical residues found individually to be responsible for loss of function due to the inability of ATP to bind the expressed receptor were then mapped to different sides of the model of the large extracellular domain. As an example, Arg 307 and Lys 311 (of SEQ ID No: 1) were on one side of the ECD while Lys193, Arg 294, His 201 and Phe 275 (of SEQ ID No: 1) were on the other side of the ECD at a distance of approximately 30 Angstroms.

This finding suggested that the assembly of monomers required close association in three dimensions between the different clusters of essential amino acids. Modelling of a trimer in which the residues were close in conformational space resulted in a model in which epitope targets on adjacent monomers was suggested. We had observed that the region of 200 to 216 of SEQ ID No: 1 (herein E200) is exposed in non-functional P2X$_7$ since only those non functional receptors could bind an antibody raised against E200. We had also observed that the region of 297 to 313 of SEQ ID No: 1 (herein E300) is exposed in non functional P2X$_7$ as only those non functional receptors could bind an antibody raised against E300. According to our modelling, these epitopes are adjacent in conformational space in the assembled trimer model.

To test the accuracy of the model of the assembled receptor, although unknown by X-ray diffraction of NMR analysis, a model of the interface consisting of exposed residues able to bind an antibody specific for the non-functional form of the receptor was devised. Elements of the E200 and E300 regions present on adjacent monomer faces were selected and spaced according to the model, this spacing being ideally 10 Angstroms. The orientation and spacing of the proposed interface accessible in non-functional receptors was the basis for the construction of the composite peptide target described below.

Presentation of the E200 region only occurs when the Pro210 residue (of SEQ ID No: 1) is in cis. Locking this residue in trans results in antibodies unable to bind to the receptor as the E200 region is not exposed. Locking Pro 210 in trans is consistent with the structure pertaining to functional receptors. Functional receptors have a unique (single) conformation. All residues exposed on the surface of functional residues are able to contribute to epitopes that are ideally avoided if specific antibodies are to be raised to bind to non-functional receptors for applications that include therapeutic targeting of non-functional receptors that do not cross-react with functional receptors. When Pro 210 is in trans then the residues in the E200 region are hidden from binding antibody by the correct formation of the ATP binding site formed by the correct packing of the P2X$_7$ monomers. Only in cis are these residues exposed to the selective antibodies able to differentiate between functional and non-functional trimers. The antibodies developed against the non-functional trimers targeting the monomer interface and binding to residues on both opposing faces can be described as trimer-specific binders, since binding to monomers is reduced approximately 50-fold.

EXAMPLE 2

Peptide Design

Specific selection of the composite peptide forming an accessible interface between monomers in the non-functional P2X$_7$ receptors involved reducing the lengths on each of the E200 and E300 regions in order to select for antibodies able to bridge between monomers over those selected for binding to one or other monomer face i.e. E200 or E300. For that reason the E200 region was reduced in length from 200-216 to 200-211 (of SEQ ID No: 1), a region still capable of simultaneous of binding two antibodies, and the E300 region was further reduced from 297-313 to 296-306 (of SEQ ID No: 1) to favour antibodies bridging E200 and E300 rather than binding solely to either E200 or E300. The presence of residues 211 and 296 (of SEQ ID No: 1) were designed to complement the residues AG also added for spacing required to appropriately separate the regions in conformational space. The reduction in individual lengths of the E200 and E300 regions combined with appropriate spacing, as deduced from the guiding model, the result of 10 years work, precluded the formation of antibodies that were likely to span residues too widely separated on the receptor, leading to distortion and commensurate loss of affinity.

A composite peptide in the form of a sequence of GHNY-TTRNILPGAGAKYYKENNVEK (SEQ ID NO:10) was prepared by solid phase synthesis according to standard techniques and conjugated using a Maleimidocaproyl-N-Hydroxysuccinimide (MCS) linker.

EXAMPLE 3

Generation of Monoclonal Antibodies

3.1 Methodology

Mice were inoculated with various composite peptides as described above in the form of 200/300-peptide conjugated to diphtheria toxoid. One peptide had the sequence: GHNYT-TRNILPGAGAKYYKENNVEK (SEQ ID NO:10). Prior to final boost, animals were screened for activity and best animals were boosted then sacrificed and spleen removed. Spleen cells were isolated and fused to Sp2/0 fusion partner cell line at a ratio of no less than 1:2 and no greater than 1:5 depending on format used. Left over spleen cells were cultured in medium for 3 days and supernatant kept for use as a positive control in the assay system.

Fusion 1—Composite E200/E300, using 96 well plates, 1 plate with macrophage feeder layers other 4 with conditioned medium only.

Macrophage plates were numbered 5 and 10.

Hybridisation Procedure

1. Make fusion tube 1 up to 50 mls with EBSS, spin at 600 rpm for 8 mins.
2. Remove supernatant from tube 1, +10 ml EBSS, mix, +15 ml EBSS.

Fusion tube 2, step 1.

Spin tubes 1&2 at 600 rpm for 8 mins.

3. Fusion tube 2 as for step 2, fusion tube 3 as for step 1.

Spin tubes 2&3 at 600 rpm for 8 mins.

4. Fusion tube 1, remove supernatant and tap tube to loosen pellet.

Set timer for 8 mins.

Add 0.8 ml PEG mixture in a 1 ml pipette, dropwise over 1 min, mixing gently.

Transfer tube to waterbath for 1 min.

Add 1 ml of I no hepes, in a 1 ml pipette, dropwise over 1 min, mixing gently.

Add 20 ml of I no hepes, dropwise from a 10 ml pipette, over 5 mins, mixing gently.

5. Tube 3 as for step 2 then spin tubes 1&3 together.
6. Tube 2 as step 4.
7. Tube 1, remove supernatant, add 10 ml Isc(+20% FBSI)+/−HAT, Resuspend, add another 30 ml.

8. Spin tubes 1 & 2 together.
9. Tube 3 as for step 4.
10. Tube 1; remove supernatant, resuspend in 10 ml Isc (+20% FBSI)+HAT and load 0.05 ml per well for 24 well format or resuspend in 40 mls and load 0.1 ml per well for 96 well format. Load 0.05 ml per well of first eight trays—24 well, 0.1 ml per well of first 4 trays—96 well.
11. Tube 2 as for step 7, tube 3 as for step 4, continuing process until all tubes loaded into trays.

ELISAS

Epitopes were coated to a PVC (polyvinyl chloride) plate and used to capture antibodies from cell supernatants. Unknowns were compared to a known positive and negative control.

EP200/300 with BSA carrier protein attached was used to coat ELISA plates for testing.

Supernatant Testing

As wells became confluent, removed all but 0.05 ml of media to a sample tube or plate.

Tested for antibody production, expanded positives, discarded negatives.

+ve's expanded out into 25 cm flasks containing 2 ml of media and left upright.

Expand to 4 mls, 2×4 mls, 2×75 cm flasks (12 ml). Expand volume to 30 ml/flask. Stocks were frozen when confluent.

Retested supernatants on freezing.

Standard Protocol Used Throughout all ELISA Assays.

Epitopes coated at 1 ug/ml concentration, diluted in PBS, 50 ul/well-shaker at RT o'night.

Wells rinsed with PBS (No Ca/Mg)

Wells blocked 1 hr with 0.1% Ovalbumin in PBS, 200 ul/well

Rinsed PBS

Supernatants to be screened (in duplicates), 50 ul/well-shaker for 2 hr at RT

Rinse 3×PBS

Rabbit anti Mouse HRP, 1/1000 in block, 50 ul/well-shaker for 1.5 hrs at RT

Rinse 4×PBS

Substrate Sigma ABTS (2,2'-Azino-bis(3-Ethylbenzthiazoline-6-Sulfonic acid Diammonium Salt) at 1.1 mg/ml in 0.05M Citrate+2 ul of Hydrogen Peroxide/10 ml to Activate—made up fresh.

Add ABTS to wells for 30 mins, 100 ul/well, stop with 25 ul/well of 5% Oxalic acid Read at Test wavelength 405/Reference 490 nm 3.2 Results Yield was very low in all plates except those containing macrophages. Three rounds of ELISA screening identified 37 clones secreting a specificity against the composite peptide. Many of these clones died out or stopped secreting. Those that survived were expanded and frozen to 5 ampoules. Serology, including cross reactivity with E200 and E300 was determined in the following Example.

EXAMPLE 4

Serological Characterisation of Antibodies

Antibodies raised against composite peptide were screened against peptides having the sequence of the E200 or E300 regions. Although able to bind to these targets, antibodies were identified as having preferred binding to the composite peptide 4.1 Testing for Cross Reactivity The antibodies generated from Example 3 were screened using ELISA as described above against either the composite peptide (COMP), U140 (a peptide having a sequence of an epitope that is found on both functional and non functional receptors), 200 (a peptide having the sequence of the E200 region), 300 (a peptide having the sequence of the E300 region) and U80 (a peptide having a sequence of an epitope that is found on both functional and non functional receptors). The results are shown in the following table and FIG. 9.

The U80 cross reactivity is probably due to DT tag as animals were immunized with DT tag and U80 used in ELISA had DT tag.

|  | T/C supn | BSA | | COMP | | U140 | | 200 | | 300 | | U80 | |
|---|---|---|---|---|---|---|---|---|---|---|---|---|---|
| 20 mins | 2A11 | 0.125 | 0.137 | 3.625 | 3.602 | 0.17 | 0.508 | 0.138 | 0.194 | 0.144 | 0.186 | 0.181 | 0.154 |
|  | 2F6 | 0.236 | 0.26 | 1.332 | 1.323 | 1.615 | 1.612 | 1.371 | 1.402 | 1.405 | 1.411 | 1.133 | 0.922 |
|  | 3D6 | 0.326 | 0.335 | 1.293 | 1.219 | 1.563 | 1.427 | 1.014 | 1.037 | 1.123 | 1.109 | 0.99 | 1.079 |
|  | 4F5 | 0.122 | 0.121 | 3.265 | 3.503 | 0.141 | 0.139 | 0.127 | 0.124 | 0.155 | 0.139 | 0.132 | 0.143 |
| Comp | 5C5 | 0.12 | 0.122 | 0.163 | 0.166 | 0.155 | 0.162 | 0.14 | 0.145 | 0.143 | 0.146 | 0.158 | 0.182 |
|  | 5C8 | 0.155 | 0.157 | 0.256 | 0.27 | 0.315 | 0.304 | 0.234 | 0.214 | 0.241 | 0.244 | 0.378 | 0.404 |
|  | 5D5 | 0.122 | 0.121 | 0.814 | 0.801 | 0.136 | 0.132 | 0.133 | 0.137 | 0.132 | 0.126 | 0.133 | 0.137 |
|  | 5F3 | 0.125 | 0.123 | 3.531 | 3.57 | 0.165 | 0.157 | 0.139 | 0.175 | 0.149 | 0.146 | 0.152 | 0.223 |
|  | 5F5 | 0.292 | 0.283 | 1.013 | 1.04 | 1.155 | 1.215 | 0.93 | 0.832 | 0.978 | 0.903 | 1.034 | 1.049 |
|  | Isc | 0.126 | 0.122 | 0.144 | 0.114 | 0.142 | 0.164 | 0.129 | 0.128 | 0.128 | 0.179 | 0.15 | 0.49 |
|  | Comp + ve | 0.163 | 0.165 | 3.607 | 3.613 | 3.62 | 3.59 | 2.678 | 2.501 | 2.707 | 2.916 | 3.597 | 3.565 |

|  |  | BSA | Comp | U140 | 200 | 300 | U80 |
|---|---|---|---|---|---|---|---|
| MEANS | 2A11 | 0.131 | 1.881 | 3.614 | 1.886 | 0.339 | 0.323 |
|  | 2F6 | 0.248 | 0.796 | 1.328 | 1.469 | 1.614 | 1.492 |
|  | 3D6 | 0.331 | 0.814 | 1.256 | 1.391 | 1.495 | 1.221 |
|  | 4F5 | 0.122 | 1.693 | 3.384 | 1.822 | 0.140 | 0.133 |
|  |  | 0.000 | 0.000 | 0.000 | 0.000 | 0.000 | 0.000 |
| Comp | 5C5 | 0.121 | 0.143 | 0.165 | 0.161 | 0.159 | 0.151 |
|  | 5C8 | 0.156 | 0.207 | 0.263 | 0.293 | 0.310 | 0.269 |
|  | 5D5 | 0.122 | 0.468 | 0.808 | 0.469 | 0.134 | 0.133 |
|  | 5F3 | 0.124 | 1.827 | 3.551 | 1.868 | 0.161 | 0.148 |
|  | 5F5 | 0.288 | 0.648 | 1.027 | 1.098 | 1.185 | 1.073 |
|  | Isc | 0.124 | 0.133 | 0.129 | 0.128 | 0.153 | 0.147 |
|  | Comp + ve | 0.164 | 1.886 | 3.610 | 3.617 | 3.605 | 3.134 |

EXAMPLE 5

Binding of Monoclonal Antibody 2F6 to Non Functional P2X on Live Tumour Cells The purified antibodies of the invention were analysed for binding to human tumour cell lines expressing the non functional $P2X_7$ and human haemopoietic cells expressing the functional $P2X_7$ by fluorescence activated cell sorter (FACS) analysis. Table 6 summarises the binding of one monoclonal antibody (MAb) 2F6 to these cells. FACS analysis demonstrated binding of MAb 2F6 to the prostate tumour cell line PC3, with a mean fluorescence intensity (MFI) of 334.62 compared to an MFI of 27.87 for the negative control antibody. Binding of MAb 2F6 to the breast tumour cell line MCF-7, was also observed, albeit weaker (MFIs of 160.3 and 50.4 for 2F6 and 3D6 control, respectively). However, virtually no binding was detected to the human lymphocytes tested (Table 6). FIG. 8 illustrates results from subsequent FACS analysis experiments and similarly demonstrates the binding of MAb 2F6 to the PC3 prostate tumour cell line and the MCF-7 breast tumour cell line, but not to the human lymphocyte sample.

TABLE 6

FACS Analysis of Binding of MAb 2F6 to Tumour Cell Lines and Human Lymphocytes

| | PC3 Prostate Tumour Cell Line | | MCF-7 Breast Tumour Cell Line | | Human Lymphocytes | |
|---|---|---|---|---|---|---|
| MAb | Mean Fluorescence Intensity (MFI) | Percent Cells Positive | Mean Fluorescence Intensity (MFI) | Percent Cells Positive | Mean Fluorescence Intensity (MFI) | Percent Cells Positive |
| IgM Negative Control (3D6) | 27.87 | 1 | 50.40 | 0 | 17.68 | 0 |
| HLA (W6/32) Positive Control | NT* | NT | 1667.92 | 87 | 3897.33 | 100 |
| 2F6 | 334.62 | 47 | 160.30 | 5 | 22.34 | 1 |

*Not tested

It will be understood that the invention disclosed and defined in this specification extends to all alternative combinations of two or more of the individual features mentioned or evident from the text or drawings. All of these different combinations constitute various alternative aspects of the invention.

---

The claims defining the invention are as follows:

1. An isolated antibody that binds to an epitope of a P2X$_7$ receptor
   the epitope being formed of:
   a first region comprising amino acid residues 200 to 211 of SEQ ID NO:1 from a first monomer of a P2X$_7$ receptor; and
   a second region comprising amino acid residues 296 to 306 of SEQ ID NO:1 from a second monomer of the receptor;
   wherein the first and second regions are formed in the receptor by cis isomerisation of a residue at position 210 of SEQ ID No: 1 of a monomer of the receptor;
   and wherein the first and second regions are arranged adjacent each other in the receptor thereby permitting binding of an antigen binding site of the antibody to the first and second regions forming the epitope.

2. The antibody of claim 1, wherein the antibody is selected from the group consisting of a polyclonal antibody, a monoclonal antibody, a recombinant antibody, a humanized antibody, a human antibody and an antigen binding fragment of each antibody type.

3. The antibody of claim 1, wherein the antibody is in the form selected from the group consisting of Fab, Fab', F(ab')2, scFv, Fd, Fv fragments, diabodies, linear antibodies, single-chain antibody molecules and multispecific antibodies formed from antibody fragments.

4. The antibody of claim 1, wherein the antibody is bivalent or bispecific.

5. The antibody claim 1, wherein antibody is in the form of a dimer, trimer or other higher-order multimer.

6. A method for determining whether an individual has a cancer comprising cancer cells comprising a P2X$_7$ receptor, the method comprising contacting a sample from the subject with the antibody of claim 1 and detecting binding of the antibody to the sample; wherein detection of an immune complex formed from the binding of the antibody identifies the individual as having cancer.

7. The method of claim 6, wherein the antibody is selected from the group consisting of a polyclonal antibody, a monoclonal antibody, a recombinant antibody, a humanized antibody, a human antibody and an antigen binding fragment of each antibody type.

8. The method of claim 6, wherein the antibody is in the form selected from the group consisting of Fab, Fab', F(ab')2, scFv, Fd, Fv fragments, diabodies, linear antibodies, single-chain antibody molecules and multispecific antibodies formed from antibody fragments.

9. The method of claim 6, wherein the antibody is bivalent or bispecific.

10. The method claim 6, wherein antibody is in the form of a dimer, trimer or other higher-order multimer.

11. A method for treating an individual having a cancer comprising cancer cells comprising a P2X$_7$ receptor, the method comprising administering the antibody of claim 1 to the individual.

12. The method of claim 11, wherein the antibody is selected from the group consisting of a polyclonal antibody, a monoclonal antibody, a recombinant antibody, a humanized antibody, a human antibody and an antigen binding fragment of each antibody type.

13. The method of claim 11, wherein the antibody is in the form selected from the group consisting of Fab, Fab', F(ab')2, scFv, Fd, Fv fragments, diabodies, linear antibodies, single-chain antibody molecules and multispecific antibodies formed from antibody fragments.

14. The method of claim 11, wherein the antibody is bivalent or bispecific.

15. The method claim 11, wherein antibody is in the form of a dimer, trimer or other higher-order multimer.

* * * * *

SEQUENCE LISTING

```
<160> NUMBER OF SEQ ID NOS: 10

<210> SEQ ID NO 1
<211> LENGTH: 595
<212> TYPE: PRT
<213> ORGANISM: Homo sapiens

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125
```

```
Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Ala
                    165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                    245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
                275                 280                 285

Pro Gly Tyr Asn Phe Arg Tyr Ala Lys Tyr Tyr Lys Glu Asn Asn Val
                290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                    325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
                355                 360                 365

Pro Trp Cys Lys Cys Gln Pro Cys Val Val Asn Glu Tyr Tyr Tyr
                370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                    405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                    485                 490                 495

Leu Cys Cys Arg Lys Lys Pro Gly Ala Cys Ile Thr Thr Ser Glu Leu
                500                 505                 510

Phe Arg Lys Leu Val Leu Ser Arg His Val Leu Gln Phe Leu Leu Leu
                515                 520                 525

Tyr Gln Glu Pro Leu Leu Ala Leu Asp Val Asp Ser Thr Asn Ser Arg
                530                 535                 540

Leu Arg His Cys Ala Tyr Arg Cys Tyr Ala Thr Trp Arg Phe Gly Ser
545                 550                 555                 560
```

```
Gln Asp Met Ala Asp Phe Ala Ile Leu Pro Ser Cys Cys Arg Trp Arg
            565                 570                 575
Ile Arg Lys Glu Phe Pro Lys Ser Glu Gly Gln Tyr Ser Gly Phe Lys
            580                 585                 590
Ser Pro Tyr
        595

<210> SEQ ID NO 2
<211> LENGTH: 9
<212> TYPE: PRT
<213> ORGANISM: Homo sapiens

<400> SEQUENCE: 2

His Asn Tyr Thr Thr Arg Asn Ile Leu
1               5

<210> SEQ ID NO 3
<211> LENGTH: 10
<212> TYPE: PRT
<213> ORGANISM: Homo sapiens

<400> SEQUENCE: 3

Gly His Asn Tyr Thr Thr Arg Asn Ile Leu
1               5                   10

<210> SEQ ID NO 4
<211> LENGTH: 13
<212> TYPE: PRT
<213> ORGANISM: Homo sapiens

<400> SEQUENCE: 4

Asp Phe Pro Gly His Asn Tyr Thr Thr Arg Asn Ile Leu
1               5                   10

<210> SEQ ID NO 5
<211> LENGTH: 209
<212> TYPE: PRT
<213> ORGANISM: Homo sapiens

<400> SEQUENCE: 5

Met Pro Ala Cys Cys Ser Cys Ser Asp Val Phe Gln Tyr Glu Thr Asn
1               5                   10                  15
Lys Val Thr Arg Ile Gln Ser Met Asn Tyr Gly Thr Ile Lys Trp Phe
            20                  25                  30
Phe His Val Ile Ile Phe Ser Tyr Val Cys Phe Ala Leu Val Ser Asp
            35                  40                  45
Lys Leu Tyr Gln Arg Lys Glu Pro Val Ile Ser Ser Val His Thr Lys
        50                  55                  60
Val Lys Gly Ile Ala Glu Val Lys Glu Glu Ile Val Glu Asn Gly Val
65                  70                  75                  80
Lys Lys Leu Val His Ser Val Phe Asp Thr Ala Asp Tyr Thr Phe Pro
                85                  90                  95
Leu Gln Gly Asn Ser Phe Phe Val Met Thr Asn Phe Leu Lys Thr Glu
            100                 105                 110
Gly Gln Glu Gln Arg Leu Cys Pro Glu Tyr Pro Thr Arg Arg Thr Leu
        115                 120                 125
Cys Ser Ser Asp Arg Gly Cys Lys Lys Gly Trp Met Asp Pro Gln Ser
130                 135                 140
Lys Gly Ile Gln Thr Gly Arg Cys Val Val His Glu Gly Asn Gln Lys
145                 150                 155                 160
```

```
Thr Cys Glu Val Ser Ala Trp Cys Pro Ile Glu Ala Val Glu Glu Ala
            165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
            195                 200                 205

Leu

<210> SEQ ID NO 6
<211> LENGTH: 49
<212> TYPE: PRT
<213> ORGANISM: Homo sapiens

<400> SEQUENCE: 6

Lys Thr Thr Asn Val Ser Leu Tyr Pro Gly Tyr Asn Phe Arg Tyr Ala
1               5                   10                  15

Lys Tyr Tyr Lys Glu Asn Asn Val Glu Lys Arg Thr Leu Ile Lys Val
            20                  25                  30

Phe Gly Ile Arg Phe Asp Ile Leu Val Phe Gly Thr Gly Lys Phe
        35                  40                  45

Asp

<210> SEQ ID NO 7
<211> LENGTH: 17
<212> TYPE: PRT
<213> ORGANISM: Homo sapiens

<400> SEQUENCE: 7

Lys Tyr Tyr Lys Glu Asn Asn Val Glu Lys Arg Thr Leu Ile Lys Val
1               5                   10                  15

Phe

<210> SEQ ID NO 8
<211> LENGTH: 11
<212> TYPE: PRT
<213> ORGANISM: Homo sapiens

<400> SEQUENCE: 8

Gly His Asn Tyr Thr Thr Arg Asn Ile Leu Pro
1               5                   10

<210> SEQ ID NO 9
<211> LENGTH: 11
<212> TYPE: PRT
<213> ORGANISM: Homo sapiens

<400> SEQUENCE: 9

Ala Lys Tyr Tyr Lys Glu Asn Asn Val Glu Lys
1               5                   10

<210> SEQ ID NO 10
<211> LENGTH: 25
<212> TYPE: PRT
<213> ORGANISM: Homo sapiens

<400> SEQUENCE: 10

Gly His Asn Tyr Thr Thr Arg Asn Ile Leu Pro Gly Ala Gly Ala Lys
1               5                   10                  15

Tyr Tyr Lys Glu Asn Asn Val Glu Lys
            20                  25
```